United States Patent [19]
Weinshank et al.

[11] Patent Number: 5,882,855
[45] Date of Patent: Mar. 16, 1999

[54] DNA ENCODING A HUMAN DOPAMINE $D_1$ RECEPTOR AND USES THEREOF

[75] Inventors: Richard L. Weinshank, New York, N.Y.; Paul R. Hartig, Kinnelon, N.J.

[73] Assignee: Synaptic Pharmaceutical Corporation, Paramus, N.J.

[21] Appl. No.: 969,267

[22] PCT Filed: Jul. 10, 1991

[86] PCT No.: PCT/US91/04858

§ 371 Date: Oct. 5, 1993

§ 102(e) Date: Oct. 5, 1993

[87] PCT Pub. No.: WO92/00986

PCT Pub. Date: Jan. 23, 1992

Related U.S. Application Data

[63] Continuation-in-part of Ser. No. 551,448, Jul. 10, 1990, abandoned.

[51] Int. Cl.$^6$ .................. C07K 14/705; C12N 15/12
[52] U.S. Cl. ................. 435/6; 435/7.1; 435/7.2; 435/69.1; 435/252.3; 435/320.1; 526/23.5; 530/350
[58] Field of Search ............... 435/7.2, 6, 69.1, 435/252.3, 320.1, 7.1; 530/350; 536/23.5

[56] References Cited

PUBLICATIONS

Sunahara, R.K., et al. Cloning of the gene for a human dopamine D5 receptor with higher affinity for dopamine than $D_1$. Nature 1991; 350:614–619 (Exhibit I).

Dearry et al., Nature 347:72–76, Sep. 6, 1990.

*Primary Examiner*—John Ulm
*Attorney, Agent, or Firm*—John P. White; Cooper & Dunham LLP

[57] ABSTRACT

This invention provides isolated nucleic acid molecules encoding a human dopamine $D_1$ receptor, isolated proteins which are human dopamine $D_1$ receptor, vectors comprising isolated nucleic acid molecules encoding a human dopamine $D_1$ receptor, mammalian cells comprising such vectors, antibodies directed to a human dopamine $D_1$ receptor, nucleic acid probes useful for detecting nucleic acid encoding human dopamine $D_1$ receptor, antisense oligonucleotides complementary to any sequences of a nucleic acid molecule which encodes a human dopamine $D_1$ receptor, pharmaceutical compounds related to human dopamine $D_1$ receptor, and nonhuman transgenic animals which express DNA a normal or a mutant human dopamine $D_1$ receptor. This invention further provides methods for determining ligand binding, detecting expression, drug screening, and treatment involving a human dopamine $D_1$ receptor.

19 Claims, 10 Drawing Sheets

FIG. 1A

```
         -130                  -110                   -90
          .      .      .      .      .      .      .      .      .
       GCAGCTCATGGTGACCCCCCTCTGGGCTCGAGGGTCCCTTGGCTGAGGGGGCGCATCCTC
          -70                   -50                   -30
          .      .      .      .      .      .      .      .      .
       GGGGTGCCGATGGGGCTGCCTGGGGGTCGCAGGGCTGAAGTTGGGACCGCGCACAGACCG
          -10                   10                    30
          .      .      .      .      .      .      .      .      .
       CCCCTGCAGTCCAGCCCAAATGCTGCCGCCAGGCAGCAACGGCACCGCGTACCCGGGGCA
                           M    L    P    P    G    S    N    G    T    A    Y    P    G    Q
           50                    70                    90
           .      .      .      .      .      .      .      .      .
       GTTCGCTCTATACCAGCAGCTGGCGCAGGGGAACGCCGTGGGGGGCTCGGCGGGGCACC
         F    A    L    Y    Q    Q    L    A    Q    G    N    A    V    G    G    S    A    G    A    P
          110                   130                   150
           .      .      .      .      .      .      .      .      .
       GCCACTGGGGCCCTCACAGGTGGTCACCGCCTGCCTGCTGACCCTACTCATCATCTGGAC
         P    L    G    P    S    Q    V    V    T    A    C    L    L    T    L    L    I    I    W    T
          170                   190                   210
           .      .      .      .      .      .      .      .      .
       CCTGCTGGGCAACGTGCTGGTGTGCGCAGCCATCGTGCGGAGCCGCCACCTGCGCGCCAA
         L    L    G    N    V    L    V    C    A    A    I    V    R    S    R    H    L    R    A    N
          230                   250                   270
           .      .      .      .      .      .      .      .      .
       CATGACCAACGTCTTCATCGTGTCTCTGGCCGTGTCAGACCTTTTCGTGGCGCTGCTGGT
         M    T    N    V    F    I    V    S    L    A    V    S    D    L    F    V    A    L    L    V
```

FIG. 1B

```
           290                      310                       330
            .        .        .      .        .        .       .
CATGCCCTGGAAGGCAGTCGCCGAGGTGGCCGGTTACTGGCCCTTTGGAGCGTTCTGCGA
 M  P  W  K  A  V  A  E  V  A  G  Y  W  P  F  G  A  F  C  D
           350                      370                       390
            .        .        .      .        .        .       .
CGTCTGGGTGGCCTTCGACATCATGTGCTCCACTGCCTCCATCCTGAACCTGTGCGTCAT
 V  W  V  A  F  D  I  M  C  S  T  A  S  I  L  N  L  C  V  I
           410                      430                       450
            .        .        .      .        .        .       .
CAGCGTGGACCGCTACTGGGCCATCTCCAGGCCCTTCCGCTACAAGCGCAAGATGACTCA
 S  V  D  R  Y  W  A  I  S  R  P  F  R  Y  K  R  K  M  T  Q
           470                      490                       510
            .        .        .      .        .        .       .
GCGCATGGCCTTGGTCATGGTCGGCCTGGCATGGACCTTGTCCATCCTCATCTCCTTCAT
 R  M  A  L  V  M  V  G  L  A  W  T  L  S  I  L  I  S  F  I
           530                      550                       570
            .        .        .      .        .        .       .
TCCGGTCCAGCTCAACTGGCACAGGGACCAGGCGGCCTCTTGGGGCGGGCTGGACCTGCC
 P  V  Q  L  N  W  H  R  D  Q  A  A  S  W  G  G  L  D  L  P
           590                      610                       630
            .        .        .      .        .        .       .
AAACAACCTGGCCAACTGGACGCCCTGGGAGGAGGACTTTTGGGAGCCCGACGTGAATGC
 N  N  L  A  N  W  T  P  W  E  E  D  F  W  E  P  D  V  N  A
           650                      670                       690
            .        .        .      .        .        .       .
AGAGAACTGTGACTCCAGCCTGAATCGAACCTACGCCATCTCTTCCTCGCTCATCAGCTT
```

FIG. 1C

```
      E   N   C   D   S   S   L   N   R   T   Y   A   I   S   S   S   L   I   S   F
              710                     730                     750
               .         .         .         .         .         .
      CTACATCCCCGTTGCCATCATGATCGTGACCTACACGCGCATCTACCGCATCGCCCAGGT
      Y   I   P   V   A   I   M   I   V   T   Y   T   R   I   Y   R   I   A   Q   V
              770                     790                     810
               .         .         .         .         .         .
      GCAGATCCGCAGGATTTCCTCCCTGGAGAGGGCCGCAGAGCACGCGCAGAGCTGCCGGAG
      Q   I   R   R   I   S   S   L   E   R   A   A   E   H   A   Q   S   C   R   S
              830                     850                     870
               .         .         .         .         .         .
      CAGCGCAGCCTGCGCGCCCGACACCAGCCTGCGCGCTTCCATCAAGAAGGAGACCAAGGT
      S   A   A   C   A   P   D   T   S   L   R   A   S   I   K   K   E   T   K   V
              890                     910                     930
               .         .         .         .         .         .
      TCTCAAGACCCTGTCGGTGATCATGGGGGTCTTCGTGTGTTGCTGGCTGCCCTTCTTCAT
      L   K   T   L   S   V   I   M   G   V   F   V   C   C   W   L   P   F   F   I
              950                     970                     990
               .         .         .         .         .         .
      CCTTAACTGCATGGTCCCTTTCTGCAGTGGACACCCTGAAGGCCCTCCGGCCGGCTTCCC
      L   N   C   M   V   P   F   C   S   G   H   P   E   G   P   P   A   G   F   P
             1010                    1030                    1050
               .         .         .         .         .         .
      CTGCGTCAGTGAGACCACCTTCGACGTCTTCGTCTGGTTCGGCTGGGCTAACTCCTCACT
      C   V   S   E   T   T   F   D   V   F   V   W   F   G   W   A   N   S   S   L
```

FIG. 1D

```
           1070                1090                1110
             .         .         .         .         .         .
        CAACCCCGTCATCTATGCCTTCAACGCCGACTTTCAGAAGGTGTTTGCCCAGCTGCTGGG
          N  P  V  I  Y  A  F  N  A  D  F  Q  K  V  F  A  Q  L  L  G
           1130                1150                1170
             .         .         .         .         .         .
        GTGCAGCCACTTCTGCTCCCGCACGCCGGTGGAGACGGTGAACATCAGCAATGAGCTCAT
          C  S  H  F  C  S  R  T  P  V  E  T  V  N  I  S  N  E  L  I
           1190                1210                1230
             .         .         .         .         .         .
        CTCCTACAACCAAGACATCGTCTTCCACAAGGAAATCGCAGCTGCCTACATCCACATGAT
          S  Y  N  Q  D  I  V  F  H  K  E  I  A  A  A  Y  I  H  M  M
           1250                1270                1290
             .         .         .         .         .         .
        GCCCAACGCCGTTACCCCCGGCAACCGGGAGGTGGACAACGACGAGGAGGAGGGTCCTTT
          P  N  A  V  T  P  G  N  R  E  V  D  N  D  E  E  E  G  P  F
           1310                1330                1350
             .         .         .         .         .         .
        CGATCGCATGTTCCAGATCTATCAGACGTCCCCAGATGGTGACCCTGTTGCTGAGTCTGT
          D  R  M  F  Q  I  Y  Q  T  S  P  D  G  D  P  V  A  E  S  V
           1370                1390                1410
             .         .         .         .         .         .
        CTGGGAGCTGGACTGCGAGGGGGAGATTTCTTTAGACAAAATAACACCTTTCACCCCGAA
          W  E  L  D  C  E  G  E  I  S  L  D  K  I  T  P  F  T  P  N
           1430                1450                1470
             .         .         .         .         .         .
        TGGATTCCATTAAACTGCATTAAGAACCCTCATGGATCTGCATAACCGCACAGACACTGA
          G  F  H  *
```

FIG. 1E

```
         1490                    1510                    1530
           .          .            .          .            .          .
CAAGCACGCACACACACGCAAATACATGCCTTTCAGTGCTGCTCCTTATCATGTGTTCTG 1550                    1570                    1590
           .          .            .          .            .          .
TGTAGTAGCTCGTGTGCTAGAACTCACCATGATGTCAGTCGAGATGCAGATCAGTGCATA 1610                    1630
           .          .            .
CTCAGTCAAGTATCAGCTACAGAGATGACAC
```

```
           III
GL-30  TASILNLCV..ISVDRYWAISRPFR  147
GL-39  TASILNLCVSVIHSVDRYWAISRPFR  149
D1     TASILDLCV..ISVDRYWAISSPFR  130
                         IV
GL-30  YKRKMTQRMALVMVGLAWTLSILIS  172
GL-39  YERKMTQRMALVMVGPAWTLSLIS   174
D1     YERKMTPKAAFILISVAWTLSVLIS  155

GL-30  FIPVQLNWHRDQAASWGGLDLPNNL  197
GL-39  FIPVQLNWHRDQAVS*GGLDLPNNL  199
D1     FIPVQLSWHKAKPTS..PSDG...   174

GL-30  ANWTPWEEDFWEPDVNAENCDSSLN  222
GL-39  ANWTPWEEAVWEPDVRAENCDSSLN  224
D1     .NATSLAE......TIDNCDSSLS   191
```

FIG. 2C

```
GL-30  RTYAISSSLISFYIPVAIMIVTYTR   247
GL-39  RTYAISSSLISFYIPMAIMIVTYTR   249
D1     RTYAISSSVISFYIPVAIMIVTYTR   216

GL-30  IYRIAQV...QIRRISSLERAAAEHAQS   271
GL-39  IYRIAQV...QICRISSLERAAAEHVQS   273
D1     IYRIAQK..QIRRIAALERAAVHAKN    240

GL-30  CRSS.....AACAPDTSLRASIK      289
GL-39  CRSS.....AGCTPDTSLRFSIK      291
D1     CQTTTGNGKPVECSQPESSFKMSFK    265

GL-30  KETKVLKTLSVIMGVFVCCWLPFFI    314
GL-39  KETKVLKPLSVIMGVFVCCWLPFFI    316
D1     RETKVLKTLSVIMGVFVCCWLPFFI    290
```

|————VII————

|  |  |  |  |  |  |  |  |  |  |  |  |  | |
|---|---|---|---|---|---|---|---|---|---|---|---|---|---|
| GL-30 | I | H | M | M | P | N | A | V | T | P | G | N | R | E | V | D | N | D | E | . | . | . | E | E | 431 |
| GL-39 | I | H | M | M | P | N | A | V | P | P | G | D | Q | E | V | D | N | D | E | . | . | . | E | E | 433 |
| D1    | . | . | I | S | K | E | C | N | L | V | Y | L | I | P | H | A | V | G | S | S | E | D | L | K | K | E | 406 |

|  |
|---|
| GL-30 | G | P | F | D | . | R | M | F | Q | I | Y | Q | T | S | P | D | G | D | P | V | A | E | S | V | W | 455 |
| GL-39 | S | P | F | D | . | R | M | S | Q | I | Y | Q | T | S | P | D | G | D | P | V | A | E | S | V | * | 457 |
| D1    | A | A | G | I | A | R | P | L | E | K | L | . | . | S | P | . | . | . | . | . | A | L | S | V | I | 424 |

|  |
|---|
| GL-30 | E | L | D | C | E | G | E | I | S | L | D | K | I | T | P | F | T | P | N | G | F | H | * | 477 |
| GL-39 | E | L | D | C | E | G | E | I | S | L | D | K | I | T | P | F | T | P | N | G | F | H | * | 480 |
| D1    | . | L | D | Y | D | T | D | V | S | L | E | K | I | Q | P | I | T | Q | N | G | Q | M | P | T | * | 447 |

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1771 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 140..1573

( x i ) SEQUENCE DESCRIPTION: SEQ ID NO:1:

```
GCAGCTCATG   GTGACCCCCC   TCTGGGCTCG   AGGGTCCCTT   GGCTGAGGGG   GCGCATCCTC           60
```

```
GGGGTGCCGA TGGGGCTGCC TGGGGGTCGC AGGGCTGAAG TTGGGACCGC GCACAGACCG         120

CCCCTGCAGT CCAGCCCAA ATG CTG CCG CCA GGC AGC AAC GGC ACC GCG TAC         172
                    Met Leu Pro Pro Gly Ser Asn Gly Thr Ala Tyr
                     1               5                   10

CCG GGG CAG TTC GCT CTA TAC CAG CAG CTG GCG CAG GGG AAC GCC GTG         220
Pro Gly Gln Phe Ala Leu Tyr Gln Gln Leu Ala Gln Gly Asn Ala Val
             15              20                  25

GGG GGC TCG GCG GGG GCA CCG CCA CTG GGG CCC TCA CAG GTG GTC ACC         268
Gly Gly Ser Ala Gly Ala Pro Pro Leu Gly Pro Ser Gln Val Val Thr
             30              35                  40

GCC TGC CTG CTG ACC CTA CTC ATC ATC TGG ACC CTG CTG GGC AAC GTG         316
Ala Cys Leu Leu Thr Leu Leu Ile Ile Trp Thr Leu Leu Gly Asn Val
             45              50                  55

CTG GTG TGC GCA GCC ATC GTG CGG AGC CGC CAC CTG CGC GCC AAC ATG         364
Leu Val Cys Ala Ala Ile Val Arg Ser Arg His Leu Arg Ala Asn Met
 60              65              70                  75

ACC AAC GTC TTC ATC GTG TCT CTG GCC GTG TCA GAC CTT TTC GTG GCG         412
Thr Asn Val Phe Ile Val Ser Leu Ala Val Ser Asp Leu Phe Val Ala
             80              85                  90

CTG CTG GTC ATG CCC TGG AAG GCA GTC GCC GAG GTG GCC GGT TAC TGG         460
Leu Leu Val Met Pro Trp Lys Ala Val Ala Glu Val Ala Gly Tyr Trp
             95              100                 105

CCC TTT GGA GCG TTC TGC GAC GTC TGG GTG GCC TTC GAC ATC ATG TGC         508
Pro Phe Gly Ala Phe Cys Asp Val Trp Val Ala Phe Asp Ile Met Cys
         110             115                 120

TCC ACT GCC TCC ATC CTG AAC CTG TGC GTC ATC AGC GTG GAC CGC TAC         556
Ser Thr Ala Ser Ile Leu Asn Leu Cys Val Ile Ser Val Asp Arg Tyr
 125                 130                 135

TGG GCC ATC TCC AGG CCC TTC CGC TAC AAG CGC AAG ATG ACT CAG CGC         604
Trp Ala Ile Ser Arg Pro Phe Arg Tyr Lys Arg Lys Met Thr Gln Arg
140                 145                 150                 155

ATG GCC TTG GTC ATG GTC GGC CTG GCA TGG ACC TTG TCC ATC CTC ATC         652
Met Ala Leu Val Met Val Gly Leu Ala Trp Thr Leu Ser Ile Leu Ile
                 160             165                 170

TCC TTC ATT CCG GTC CAG CTC AAC TGG CAC AGG GAC CAG GCG GCC TCT         700
Ser Phe Ile Pro Val Gln Leu Asn Trp His Arg Asp Gln Ala Ala Ser
             175             180                 185

TGG GGC GGG CTG GAC CTG CCA AAC AAC CTG GCC AAC TGG ACG CCC TGG         748
Trp Gly Gly Leu Asp Leu Pro Asn Asn Leu Ala Asn Trp Thr Pro Trp
         190                 195                 200

GAG GAG GAC TTT TGG GAG CCC GAC GTG AAT GCA GAG AAC TGT GAC TCC         796
Glu Glu Asp Phe Trp Glu Pro Asp Val Asn Ala Glu Asn Cys Asp Ser
 205                 210                 215

AGC CTG AAT CGA ACC TAC GCC ATC TCT TCC TCG CTC ATC AGC TTC TAC         844
Ser Leu Asn Arg Thr Tyr Ala Ile Ser Ser Ser Leu Ile Ser Phe Tyr
220                 225                 230                 235

ATC CCC GTT GCC ATC ATG ATC GTG ACC TAC ACG CGC ATC TAC CGC ATC         892
Ile Pro Val Ala Ile Met Ile Val Thr Tyr Thr Arg Ile Tyr Arg Ile
                 240                 245                 250

GCC CAG GTG CAG ATC CGC AGG ATT TCC TCC CTG GAG AGG GCC GCA GAG         940
Ala Gln Val Gln Ile Arg Arg Ile Ser Ser Leu Glu Arg Ala Ala Glu
                 255                 260                 265

CAC GCG CAG AGC TGC CGG AGC AGC GCA GCC TGC GCG CCC GAC ACC AGC         988
His Ala Gln Ser Cys Arg Ser Ser Ala Ala Cys Ala Pro Asp Thr Ser
             270                 275                 280

CTG CGC GCT TCC ATC AAG AAG GAG ACC AAG GTT CTC AAG ACC CTG TCG        1036
Leu Arg Ala Ser Ile Lys Lys Glu Thr Lys Val Leu Lys Thr Leu Ser
 285                 290                 295

GTG ATC ATG GGG GTC TTC GTG TGT TGC TGG CTG CCC TTC TTC ATC CTT        1084
Val Ile Met Gly Val Phe Val Cys Cys Trp Leu Pro Phe Phe Ile Leu
```

```
300                     305                     310                     315
AAC TGC ATG GTC CCT TTC TGC AGT GGA CAC CCT GAA GGC CCT CCG GCC    1132
Asn Cys Met Val Pro Phe Cys Ser Gly His Pro Glu Gly Pro Pro Ala
            320             325                     330

GGC TTC CCC TGC GTC AGT GAG ACC ACC TTC GAC GTC TTC GTC TGG TTC    1180
Gly Phe Pro Cys Val Ser Glu Thr Thr Phe Asp Val Phe Val Trp Phe
            335             340                     345

GGC TGG GCT AAC TCC TCA CTC AAC CCC GTC ATC TAT GCC TTC AAC GCC    1228
Gly Trp Ala Asn Ser Ser Leu Asn Pro Val Ile Tyr Ala Phe Asn Ala
            350             355                     360

GAC TTT CAG AAG GTG TTT GCC CAG CTG CTG GGG TGC AGC CAC TTC TGC    1276
Asp Phe Gln Lys Val Phe Ala Gln Leu Leu Gly Cys Ser His Phe Cys
    365                 370                     375

TCC CGC ACG CCG GTG GAG ACG GTG AAC ATC AGC AAT GAG CTC ATC TCC    1324
Ser Arg Thr Pro Val Glu Thr Val Asn Ile Ser Asn Glu Leu Ile Ser
380                 385                     390                 395

TAC AAC CAA GAC ATC GTC TTC CAC AAG GAA ATC GCA GCT GCC TAC ATC    1372
Tyr Asn Gln Asp Ile Val Phe His Lys Glu Ile Ala Ala Ala Tyr Ile
                400                     405                 410

CAC ATG ATG CCC AAC GCC GTT ACC CCC GGC AAC CGG GAG GTG GAC AAC    1420
His Met Met Pro Asn Ala Val Thr Pro Gly Asn Arg Glu Val Asp Asn
            415                     420                 425

GAC GAG GAG GAG GGT CCT TTC GAT CGC ATG TTC CAG ATC TAT CAG ACG    1468
Asp Glu Glu Glu Gly Pro Phe Asp Arg Met Phe Gln Ile Tyr Gln Thr
        430                     435                     440

TCC CCA GAT GGT GAC CCT GTT GCT GAG TCT GTC TGG GAG CTG GAC TGC    1516
Ser Pro Asp Gly Asp Pro Val Ala Glu Ser Val Trp Glu Leu Asp Cys
        445                     450                     455

GAG GGG GAG ATT TCT TTA GAC AAA ATA ACA CCT TTC ACC CCG AAT GGA    1564
Glu Gly Glu Ile Ser Leu Asp Lys Ile Thr Pro Phe Thr Pro Asn Gly
460                     465                     470                 475

TTC CAT TAA ACTGCATTAA GAACCCTCAT GGATCTGCAT AACCGCACAG            1613
Phe His  *
ACACTGACAA GCACGCACAC ACACGCAAAT ACATGCCTTT CAGTGCTGCT CCTTATCATG  1673

TGTTCTGTGT AGTAGCTCGT GTGCTAGAAC TCACCATGAT GTCAGTCGAG ATGCAGATCA  1733

GTGCATACTC AGTCAAGTAT CAGCTACAGA GATGACAC                          1771
```

( 2 ) INFORMATION FOR SEQ ID NO:2:

( i ) SEQUENCE CHARACTERISTICS:
        ( A ) LENGTH: 477 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Pro Pro Gly Ser Asn Gly Thr Ala Tyr Pro Gly Gln Phe Ala
 1               5                  10                  15

Leu Tyr Gln Gln Leu Ala Gln Gly Asn Ala Val Gly Gly Ser Ala Gly
            20                  25                  30

Ala Pro Pro Leu Gly Pro Ser Gln Val Val Thr Ala Cys Leu Leu Thr
            35                  40                  45

Leu Leu Ile Ile Trp Thr Leu Leu Gly Asn Val Leu Val Cys Ala Ala
     50                  55                  60

Ile Val Arg Ser Arg His Leu Arg Ala Asn Met Thr Asn Val Phe Ile
 65                  70                  75                  80

Val Ser Leu Ala Val Ser Asp Leu Phe Val Ala Leu Leu Val Met Pro
                85                  90                  95
```

| Trp | Lys | Ala | Val | Ala | Glu | Val | Ala | Gly | Tyr | Trp | Pro | Phe | Gly | Ala | Phe |
|---|---|---|---|---|---|---|---|---|---|---|---|---|---|---|---|
| | | | 100 | | | | | 105 | | | | | 110 | | |
| Cys | Asp | Val | Trp | Val | Ala | Phe | Asp | Ile | Met | Cys | Ser | Thr | Ala | Ser | Ile |
| | | | 115 | | | | 120 | | | | | 125 | | | |
| Leu | Asn | Leu | Cys | Val | Ile | Ser | Val | Asp | Arg | Tyr | Trp | Ala | Ile | Ser | Arg |
| | 130 | | | | | 135 | | | | | | 140 | | | |
| Pro | Phe | Arg | Tyr | Lys | Arg | Lys | Met | Thr | Gln | Arg | Met | Ala | Leu | Val | Met |
| 145 | | | | | 150 | | | | | 155 | | | | | 160 |
| Val | Gly | Leu | Ala | Trp | Thr | Leu | Ser | Ile | Leu | Ile | Ser | Phe | Ile | Pro | Val |
| | | | | 165 | | | | | 170 | | | | | 175 | |
| Gln | Leu | Asn | Trp | His | Arg | Asp | Gln | Ala | Ala | Ser | Trp | Gly | Gly | Leu | Asp |
| | | | 180 | | | | | 185 | | | | | 190 | | |
| Leu | Pro | Asn | Asn | Leu | Ala | Asn | Trp | Thr | Pro | Trp | Glu | Glu | Asp | Phe | Trp |
| | | | 195 | | | | | 200 | | | | | 205 | | |
| Glu | Pro | Asp | Val | Asn | Ala | Glu | Asn | Cys | Asp | Ser | Ser | Leu | Asn | Arg | Thr |
| | | | 210 | | | | 215 | | | | | 220 | | | |
| Tyr | Ala | Ile | Ser | Ser | Ser | Leu | Ile | Ser | Phe | Tyr | Ile | Pro | Val | Ala | Ile |
| 225 | | | | | 230 | | | | | 235 | | | | | 240 |
| Met | Ile | Val | Thr | Tyr | Thr | Arg | Ile | Tyr | Arg | Ile | Ala | Gln | Val | Gln | Ile |
| | | | | 245 | | | | | 250 | | | | | 255 | |
| Arg | Arg | Ile | Ser | Ser | Leu | Glu | Arg | Ala | Ala | Glu | His | Ala | Gln | Ser | Cys |
| | | | 260 | | | | | 265 | | | | | 270 | | |
| Arg | Ser | Ser | Ala | Ala | Cys | Ala | Pro | Asp | Thr | Ser | Leu | Arg | Ala | Ser | Ile |
| | | 275 | | | | | 280 | | | | | 285 | | | |
| Lys | Lys | Glu | Thr | Lys | Val | Leu | Lys | Thr | Leu | Ser | Val | Ile | Met | Gly | Val |
| | 290 | | | | | 295 | | | | | 300 | | | | |
| Phe | Val | Cys | Cys | Trp | Leu | Pro | Phe | Phe | Ile | Leu | Asn | Cys | Met | Val | Pro |
| 305 | | | | | 310 | | | | | 315 | | | | | 320 |
| Phe | Cys | Ser | Gly | His | Pro | Glu | Gly | Pro | Pro | Ala | Gly | Phe | Pro | Cys | Val |
| | | | | 325 | | | | | 330 | | | | | 335 | |
| Ser | Glu | Thr | Thr | Phe | Asp | Val | Phe | Val | Trp | Phe | Gly | Trp | Ala | Asn | Ser |
| | | | 340 | | | | | 345 | | | | | 350 | | |
| Ser | Leu | Asn | Pro | Val | Ile | Tyr | Ala | Phe | Asn | Ala | Asp | Phe | Gln | Lys | Val |
| | | 355 | | | | | 360 | | | | | 365 | | | |
| Phe | Ala | Gln | Leu | Leu | Gly | Cys | Ser | His | Phe | Cys | Ser | Arg | Thr | Pro | Val |
| | 370 | | | | | 375 | | | | | 380 | | | | |
| Glu | Thr | Val | Asn | Ile | Ser | Asn | Glu | Leu | Ile | Ser | Tyr | Asn | Gln | Asp | Ile |
| 385 | | | | | 390 | | | | | 395 | | | | | 400 |
| Val | Phe | His | Lys | Glu | Ile | Ala | Ala | Ala | Tyr | Ile | His | Met | Met | Pro | Asn |
| | | | | 405 | | | | | 410 | | | | | 415 | |
| Ala | Val | Thr | Pro | Gly | Asn | Arg | Glu | Val | Asp | Asn | Asp | Glu | Glu | Glu | Gly |
| | | | 420 | | | | | 425 | | | | | 430 | | |
| Pro | Phe | Asp | Arg | Met | Phe | Gln | Ile | Tyr | Gln | Thr | Ser | Pro | Asp | Gly | Asp |
| | | 435 | | | | | 440 | | | | | 445 | | | |
| Pro | Val | Ala | Glu | Ser | Val | Trp | Glu | Leu | Asp | Cys | Glu | Gly | Glu | Ile | Ser |
| | 450 | | | | | 455 | | | | | 460 | | | | |
| Leu | Asp | Lys | Ile | Thr | Pro | Phe | Thr | Pro | Asn | Gly | Phe | His | | | |
| 465 | | | | | 470 | | | | | 475 | | | | | |

( 2 ) INFORMATION FOR SEQ ID NO:3:

( i ) SEQUENCE CHARACTERISTICS:
        ( A ) LENGTH: 477 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Leu Pro Pro Arg Ser Asn Gly Thr Ala Tyr Pro Gly Gln Leu Ala
 1               5                  10                  15

Leu Tyr Gln Gln Leu Ala Gln Gly Asn Ala Val Gly Gly Ser Ala Gly
                 20                  25                  30

Ala Pro Pro Leu Gly Pro Val Gln Val Val Thr Ala Cys Leu Leu Thr
             35                  40                  45

Leu Leu Ile Ile Trp Thr Leu Leu Gly Asn Val Leu Met Ser Ala Ala
     50                  55                  60

Ile Val Arg Thr Arg His Leu Arg Ala Lys Met Thr Asn Val Phe Ile
 65                  70                  75                  80

Val Ser Leu Ala Val Ser Asp Leu Phe Val Ala Leu Leu Val Met Pro
                 85                  90                  95

Trp Lys Ala Val Ala Glu Val Ala Gly Tyr Trp Pro Phe Glu Ala Phe
                100                 105                 110

Cys Asp Val Trp Val Ala Phe Asp Ile Met Cys Ser Thr Ala Ser Ile
             115                 120                 125

Leu Asn Leu Cys Val Ser Val Ile Ser Val Gly Arg Tyr Trp Ala Ile
     130                 135                 140

Ser Arg Pro Phe Arg Tyr Glu Arg Lys Met Thr Gln Arg Met Ala Leu
145                 150                 155                 160

Val Met Val Gly Pro Ala Trp Thr Leu Ser Ser Leu Ile Ser Phe Ile
                165                 170                 175

Pro Val Gln Leu Asn Trp His Arg Asp Gln Ala Val Ser Gly Gly Leu
                180                 185                 190

Asp Leu Pro Asn Asn Leu Ala Asn Trp Thr Pro Trp Glu Ala Val Val
             195                 200                 205

Trp Glu Pro Asp Val Arg Ala Glu Asn Cys Asp Ser Ser Leu Asn Arg
    210                 215                 220

Thr Tyr Ala Ile Ser Ser Ser Leu Ile Asn Phe Tyr Ile Pro Met Ala
225                 230                 235                 240

Ile Met Ile Val Thr Tyr Thr Arg Ile Tyr Arg Ile Ala Gln Val Gln
                245                 250                 255

Ile Cys Arg Ile Ser Ser Leu Glu Arg Ala Ala Glu His Val Gln Ser
             260                 265                 270

Cys Arg Ser Ser Ala Gly Cys Thr Pro Asp Thr Ser Leu Arg Phe Ser
    275                 280                 285

Ile Lys Lys Glu Thr Lys Val Leu Lys Pro Leu Ser Val Ile Met Gly
                290                 295                 300

Val Phe Val Cys Cys Trp Leu Pro Phe Phe Ile Leu Asn Cys Met Val
305                 310                 315                 320

Pro Phe Arg Ser Gly His Pro Lys Gly Pro Pro Ala Gly Phe Pro Cys
                325                 330                 335

Val Ser Glu Thr Thr Phe Asp Val Phe Ile Trp Phe Cys Trp Ala Asn
             340                 345                 350

Ser Ser Leu Asn Pro Val Tyr Ala Phe Asn Ala Asp Phe Trp Lys Val
    355                 360                 365

Phe Ala Gln Leu Leu Gly Cys Ser His Val Cys Ser Arg Thr Pro Val
    370                 375                 380

Glu Thr Val Asn Ile Ser Asn Glu Leu Ile Ser Tyr Asn Gln Asp Met
385                 390                 395                 400
```

-continued

```
Val Phe His Lys Glu Ile Ala Ala Ala Cys Ile His Met Met Pro Asn
            405                 410                         415
Ala Val Pro Pro Gly Asp Gln Glu Val Asp Asn Asp Glu Glu Glu
            420             425                 430
Ser Pro Phe Asp Arg Met Ser Gln Ile Tyr Gln Thr Ser Pro Asp Gly
            435                 440                 445
Asp Pro Val Ala Glu Ser Val Glu Leu Asp Cys Glu Gly Glu Ile Ser
    450                 455                 460
Leu Asp Lys Ile Thr Pro Phe Thr Pro Asn Gly Phe His
465             470                 475
```

(2) INFORMATION FOR SEQ ID NO:4:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: D1

(xi) SEQUENCE DESCRIPTION: SEQ ID NO:4:

```
Met Arg Thr Leu Asn Thr Ser Ala Met Asp Gly Thr Gly Leu Val Val
1               5                   10                  15
Glu Arg Asp Phe Ser Val Arg Ile Leu Thr Ala Cys Phe Leu Ser Leu
            20                  25                  30
Leu Ile Leu Ser Thr Leu Leu Gly Asn Thr Leu Val Cys Ala Ala Val
            35                  40                  45
Ile Arg Phe Arg His Leu Arg Ser Lys Val Thr Asn Phe Phe Val Ile
    50                  55                  60
Ser Leu Ala Val Ser Asp Leu Leu Val Ala Val Leu Val Met Pro Trp
65                  70                  75                  80
Lys Ala Val Ala Glu Ile Ala Gly Phe Trp Pro Phe Gly Ser Phe Cys
                85                  90                  95
Asn Ile Trp Val Ala Phe Asp Ile Met Cys Ser Thr Ala Ser Ile Leu
            100                 105                 110
Asp Leu Cys Val Ile Ser Val Asp Arg Tyr Trp Ala Ile Ser Ser Pro
        115                 120                 125
Phe Arg Tyr Glu Arg Lys Met Thr Pro Lys Ala Ala Phe Ile Leu Ile
    130                 135                 140
Ser Val Ala Trp Thr Leu Ser Val Leu Ile Ser Phe Ile Pro Val Gln
145                 150                 155                 160
Leu Ser Trp His Lys Ala Lys Pro Thr Ser Pro Ser Asp Gly Asn Ala
                165                 170                 175
Thr Ser Leu Ala Glu Thr Ile Asp Asn Cys Asp Ser Ser Leu Ser Arg
            180                 185                 190
Thr Tyr Ala Ile Ser Ser Ser Val Ile Ser Phe Tyr Ile Pro Val Ala
        195                 200                 205
Ile Met Ile Val Thr Tyr Thr Arg Ile Tyr Arg Ile Ala Gln Lys Gln
    210                 215                 220
Ile Arg Arg Ile Ala Ala Leu Glu Arg Ala Ala Val His Ala Lys Asn
225                 230                 235                 240
Cys Gln Thr Thr Thr Gly Asn Gly Lys Pro Val Glu Cys Ser Gln Pro
                245                 250                 255
Glu Ser Ser Phe Lys Met Ser Phe Lys Arg Glu Thr Lys Val Leu Lys
```

-continued

|  |  |  |  |  |  |  | 260 |  |  |  | 265 |  |  |  | 270 |  |  |
|---|---|---|---|---|---|---|---|---|---|---|---|---|---|---|---|---|---|
| Thr | Leu | Ser<br>275 | Val | Ile | Met | Gly | Val<br>280 | Phe | Val | Cys | Cys | Trp<br>285 | Leu | Pro | Phe |
| Phe | Ile<br>290 | Leu | Asn | Cys | Ile | Leu<br>295 | Pro | Phe | Cys | Gly | Ser<br>300 | Gly | Glu | Thr | Gln |
| Pro<br>305 | Phe | Cys | Ile | Asp | Ser<br>310 | Asn | Thr | Phe | Asp | Val<br>315 | Phe | Val | Trp | Phe | Gly<br>320 |
| Trp | Ala | Asn | Ser | Ser<br>325 | Leu | Asn | Pro | Ile | Ile<br>330 | Tyr | Ala | Phe | Asn | Ala<br>335 | Asp |
| Phe | Arg | Lys | Ala<br>340 | Phe | Ser | Thr | Leu | Leu<br>345 | Gly | Cys | Tyr | Arg | Leu<br>350 | Cys | Pro |
| Ala | Thr | Asn<br>355 | Asn | Ala | Ile | Glu | Thr<br>360 | Val | Ser | Ile | Asn | Asn<br>365 | Asn | Gly | Ala |
| Ala | Met<br>370 | Phe | Ser | Ser | His | His<br>375 | Glu | Pro | Arg | Gly | Ser<br>380 | Ile | Ser | Lys | Glu |
| Cys<br>385 | Asn | Leu | Val | Tyr | Leu<br>390 | Ile | Pro | His | Ala | Val<br>395 | Gly | Ser | Ser | Glu | Asp<br>400 |
| Leu | Lys | Lys | Glu | Glu<br>405 | Ala | Ala | Gly | Ile | Ala<br>410 | Arg | Pro | Leu | Glu | Lys<br>415 | Leu |
| Ser | Pro | Ala | Leu<br>420 | Ser | Val | Ile | Leu | Asp<br>425 | Tyr | Asp | Thr | Asp | Val<br>430 | Ser | Leu |
| Glu | Lys | Ile | Gln | Pro | Ile | Thr | Gln | Asn | Gly | Gln | His | Pro | Thr |  |  |

DNA ENCODING A HUMAN DOPAMINE $D_1$ RECEPTOR AND USES THEREOF

This application is a continuation-in-part of U.S. Ser. No. 551,448, filed Jul. 10, 1990, now abandoned, the contents of which are hereby incorporated by reference into the present disclosure.

BACKGROUND OF THE INVENTION

Throughout this application various publications are referenced by full citations within parentheses. The disclosures of these publications in their entireties are hereby incorporated by reference in this application in order to more fully describe the state of the art to which this invention pertains.

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses. The variation in cellular response can be achieved by the association of individual receptor subtypes with different G proteins and different signalling systems. Further flexibility is provided by the ability of distinct receptors for the same ligand to activate or inhibit the same second messenger system.

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success. Similarly, the biochemical mechanisms by which these receptors transduce signals across the cell surface have been difficult to ascertain without having well-defined cell populations which express exclusively one receptor subtype.

Dopamine receptors have been classified into two subtypes, $D_1$ and $D_2$, based on their differential affinities for dopamine agonists and antagonists, and their stimulation or inhibition of adenylate cyclase (for reviews, see Kebabian, J. W. and Calne, D. B. (1979), Nature 277, 93–96; Creese, I., Sibley, D. R., Hamblin, M. W., Leff, S. E. (1983), Ann. Rev. Neurosci. 6, 43–71; Niznik, H. B. and Jarvie, K. R. (1989), Dopamine receptors. in "Receptor Pharmacology and Function", eds. Williams, M., Glennon, R., and Timmermans, P., Marcel Dekker Inc., New York, pp. 717–768). The $D_1$ receptor of the central nervous system is defined as an adenylate cyclase stimulatory receptor. The location of the prototypic $D_1$ receptor is the bovine parathyroid gland, where dopamine agonists stimulate cAMP synthesis via adenylate cyclase, accompanied by parathyroid hormone release. Dopamine-stimulated adenylate cyclase activity and parathyroid hormone release are sensitive to both GTP and cholera toxin. This suggests that the $D_1$ receptor is associated with a $G_S$ guanine nucleotide binding protein. The $D_2$ receptor, in contrast, inhibits adenylate cyclase activity, and appears to be the primary target of most neuroleptic drugs (Niznik, H. B. and Jarvie, K. R. (1989). Dopamine receptors, in "Receptor Pharmacology and Function", eds. Williams, M., Glennon, R., and Timmermans, P., Marcel Dekker Inc., New York, pp. 717–768). The prototypic $D_2$ receptor has been characterized in the anterior pituitary where it is associated with the inhibition of release of prolactin and alpha-melanocyte stimulating hormones. Recent work has shown that several different $D_1$ and $D_2$ receptor subtypes may be present in the mammalian nervous system (Andersen, P. H., Gingrich, J. A., Bates, M. D., Dearry, A., Falardeau, P., Senogles, S. E., and Caron, M. G. Trends in Pharmacolog. Sci. 11: 231 (1990)), which would suggest that a family of different proteins with pharmacological properties similar to the classically defined $D_1$ and $D_2$ receptors may exist.

Neuroleptics, in addition to their use as drugs to treat severe psychiatric illnesses, are high affinity ligands for dopamine receptors. Butyrophenones such as haloperidol and spiperone are antagonists specific for the $D_2$ receptor, while the recently developed benzazepines such as SCH-23390 and SKF-38393 are selective for the $D_1$ receptor (Niznik, H. B. and Jarvie, K. R. (1989), Dopamine receptors, in "Receptor Pharmacology and Function", eds. Williams, M., Glennon, R., and Timmermans, P., Marcel Dekker Inc., New York, pp. 717–768). High affinity $D_1$ and $D_2$ selective ligands have conclusively distinguished these receptors and made feasible characterization of the receptors in the central nervous system and peripheral tissues with radioligand binding techniques. Two types of dopamine receptors, designated $D_{A1}$ and $D_{A2}$, have been identified in the cardiovascular system and are similar in their pharmacological characteristics to the brain $D_1$ and $D_2$ receptors (Niznik, H. B. and Jarvie, K. R. (1989), Dopamine receptors, in "Receptor Pharmacology and Function", eds. Williams, M., Glennon, R., and Timmermans, P., Marcel Dekker Inc., New York, pp. 717–768). $D_{A1}$ receptors have been described in renal, mesenteric, splenic, coronary, cerebral, and pulmonary arteries and vascular beds, where dopamine elicits relaxation of vascular smooth muscle. Activation of cardiovascular $D_{A1}$ receptors appears to stimulate adenylate cyclase activity. $D_{A2}$ receptors appear to be localized on preganglionic sympathetic nerve terminals that mediate inhibition of norepinephrine release. The molecular relationships among dopamine $D_1$, $D_{A1}$, $D_2$, and $D_{A2}$ receptors are unknown.

The need for improved selectivity in the leading $D_1$ drug class, the benzazepines (e.g. SKF-38393, SCH-23390 and SCH-23982) recently became apparent when the strong cross-reactivity of these drugs with the serotonin 5-$HT_2$ receptor family was uncovered. The 5-$HT_2$ and 5-$HT_{1C}$ receptors display affinities ranging from 0.2 to 24 nM for SCH-23390 and SCH-23982 (Nicklaus, K. J., McGonigle, P., and Molinoff, P. B. (1988), J. Pharmacol. Exp. Ther. 247, 343–348; Hoyer, D. and Karpf, A. (1988), Eur. J. Pharmacol. 150, 181–184)), raising the possibility that behavioral and pharmacological effects ascribed to these drugs may, in fact, arise from serotonergic receptor interactions.

The dopamine $D_1$ receptors belong to a family of receptors which are distinguished by their seven-transmembrane configuration and their functional linkage to G-proteins. This family includes rhodopsin and related opsins (Nathans, J. and Hogness, D. S., Cell 34:807 (1983)), the $\alpha$ and $\beta$ adrenergic receptors (Dohlman, H. G., et al., Biochemistry 26:2657 (1987)), the muscarinic cholinergic receptors (Bonner, T. I., et al., Science 237:527 (1987)), the substance K neuropeptide receptor, (Masu, Y., et al., Nature 329:836 (1987)), the yeast mating factor receptors, (Burkholder, A. C. and Hartwell, L. H., Nucl. Acids Res. 13:8463(1985); Hagan, D. C., et al., Proc. Natl. Acad. Sci. USA 83:1418 (1986)); Nakayama, N. et al., EMBO J. 4:2643 (1985)), and the oncogene c-mas, (Young, et al., Cell 45:711 (1986)). Each of these receptors is thought to transduce extracellular signals by interaction with guanine nucleotide-binding (G) proteins (Dohlman, H. G., et al., Biochemistry 26:2657 (1987); Dohlman, H. G., et al., Biochemistry 27:1813 (1988); O'Dowd, B. F., et al., Ann. Rev. Neurosci., in press).

The $D_2$ receptor was recently cloned by Civelli and colleagues (Bunzow, J. R., Van Tol, H. H. M., Grandy, D. K., Albert, P., Salon, J., Christie, M., Machida, C. A., Neve, K. A., and Civelli, O. (1989), Nature 336: 783–87). This event was soon followed by the discovery of an alternatively spliced form (termed $D_{2A}$, $D_{2long}$, $D-2_{in}$, or $D_{2(444)}$) that contains an additional 29 amino acids in the third extracellular loop of this receptor (Eidne, K. A. et al. (1989), Nature 342: 865; Giros, B. et al. (1989), Nature 342: 923–26; Grandy, D. K. et al. (1989), Proc. Natl. Acad. Sci. USA 86: 9762–66; Monsma, F. J. et al. (1989), Nature 342: 926–29; Chio, C. L. et al. (1990), Nature 343: 266–69; Stormann, T. M. et al. (1990), Mol. Pharmacol. 37: 1–6). A second dopamine receptor has been cloned which exhibits significant homology to the $D_2$ receptor, both in amino acid sequence (75% transmembrane region identity) and in pharmacological properties (Sokoloff, P. et al. (1990), Nature 347: 146–51). This new receptor, termed $D_3$, is encoded by an intron-containing gene. Unlike the $D_2$ receptor, however, alternatively spliced isoforms of this receptor. have yet to be observed. The $D_3$ receptor has been shown to serve both as an autoreceptor and as a postsynaptic receptor, and has been localized to limbic areas of the brain (Sokoloff, P. et al. (1990), Nature 347: 146–51). Finally, an intronless gene, quite different in sequence and gene structure from the other two dopamine receptor genes, has been isolated and identified as a $D_1$ dopamine receptor subtype (Sunahara, R. K. et al. (1990), Nature 347: 80–83; Zhou, Q.-Y. et al. (1990), Nature 347: 76–80; Dearry, A. et al. (1990), Nature 347: 72–76; Monsma, F. J. et al. (1990), Proc. Natl. Acad. Sci. USA 87: 6723–27). This $D_1$ receptor is predominantly expressed in the rat striatum and olfactory tubercles, and has been shown to couple to stimulation of adenylate cyclase activity (Dearry et al. (1990) supra; Monsma et al. (1990) supra; Sunahara et al. (1990) supra; Zhou et al. (1990) supra. Available data on the G protein-coupled receptor superfamily suggests that the $D_1$ receptor does not exhibit strong sequence homologies to the $D_2$ receptor or the $D_3$ receptor. In general, G protein-coupled receptors of the same neurotransmitter family exhibit closest structural homology to other family members that use the same second messenger pathway. For example, examination of the physiological second messenger pathways of the serotonergic, muscarinic and adrenergic receptors has led several researchers to the conclusion that these receptors can be classified into structurally homologous subtypes that parallel their second messenger pathways (Bylund, D. B. (1988), Trends Pharmacol. Sci. 9, 356–361; Peralta, E. G., Ashkenazi, A., Winslow, J. W., Ramachandran, J., and Capon, D. J. (1988), Nature 334, 434–437; Liao, C.-F., Themmen, A. P. N., Joho, R., Barberis, C., Birnbaumer, M., and Birnbaumer, L. (1989), J. Biol. Chem. 264, 7328–7337; Hartig, P. R. (1989), Trends Pharmacol. Sci. 10, 64–69)). Interestingly, those receptors that couple to activation of adenylate cyclase appear quite distinct in structure from those that inhibit this enzyme activity.

Pharmacological and physiological data have emerged indicating the presence of further diversity within this receptor family. A $D_1$ receptor that stimulates phosphoinositide (PI) hydrolysis in rat striatum has been described (Undie, A. S., and Friedman, E. (1990), J. Pharmacol. Exp. Ther. 253: 987–92) as well as an RNA fraction from the same tissue that causes dopamine-stimulated PI hydrolysis and intracellular calcium release when injected into Xenopus oocytes (Mahan, L. C. et al. (1990), Proc. Natl. Acad. Sci. USA 87: 2196–2200). In addition, two populations of peripheral $D_1$ receptor have been described based on differential sensitivity to sulpiride and several other compounds (Andersen, P. H. et al. (1990), Eur. J. Pharmacol. 137: 291–93). Finally, pharmacological differences exist within different $D_1$ receptor tissues that couple to adenylate cyclase-coupled $D_1$ receptors. Biochemical and pharmacological data suggest further diversity in both the $D_1$ and $D_2$ receptor populations and indicate that additional dopamine receptor clones remain to be discovered (Andersen et al. (1990) supra).

SUMMARY OF THE INVENTION

This invention provides an isolated nucleic acid molecule encoding a human dopamine $D_1$ receptor.

This invention also provides an isolated protein which is a human dopamine $D_1$ receptor, an isolated protein having substantially the same amino acid sequence as the amino acid sequence shown in FIGS. 1A–1E (SEQ ID NO:1).

This invention provides a vector comprising an isolated nucleic acid molecule encoding a human dopamine $D_1$ receptor.

This invention provides a mammalian cell comprising a DNA molecule encoding a human dopamine $D_1$ receptor.

This invention provides a method for determining whether a ligand not known to be capable of binding to a human dopamine $D_1$ receptor can bind to a human dopamine $D_1$ receptor which comprises contacting a mammalian cell comprising a DNA molecule encoding a human dopamine $D_1$ receptor with the ligand under conditions permitting binding of ligands known to bind to the dopamine $D_1$ receptor, detecting the presence of any of the ligand bound to the dopamine $D_1$ receptor, and thereby determining whether the ligand binds to the dopamine $D_1$ receptor.

This invention also provides a method of screening drugs to identify drugs which specifically interact with, and bind to, the human dopamine $D_1$ receptor on the surface of a cell which comprises contacting a mammalian cell comprising a DNA molecule encoding a human dopamine $D_1$ receptor on the surface of a cell with a plurality of drugs, determining those drugs which bind to the mammalian cell, and thereby identifying drugs which specifically interact with, and bind to, the human dopamine $D_1$ receptor.

This invention provides a nucleic acid probe comprising a nucleic acid molecule of at least 15 nucleotides capable of specifically hybridizing with a sequence included within the sequence of a nucleic acid molecule encoding a human dopamine $D_1$ receptor.

This invention provides an antisense oligonucleotide having a sequence capable of binding specifically with any sequences of an mRNA molecule which encodes a human dopamine $D_1$ receptor so as to prevent translation of the mRNA molecule.

This invention provides an antibody directed to the human dopamine $D_1$ receptor.

This invention provides a transgenic nonhuman mammal expressing DNA encoding a human dopamine $D_1$ receptor. This invention also provides a transgenic nonhuman mammal expressing DNA encoding a human dopamine $D_1$ receptor so mutated as to be incapable of normal receptor activity, and not expressing native dopamine $D_1$ receptor. This invention further provides a transgenic nonhuman mammal whose genome comprises antisense DNA complementary to DNA encoding a human dopamine $D_1$ receptor so placed as to be transcribed into antisense mRNA which is complementary to mRNA encoding a dopamine $D_1$ receptor and which hybridizes to mRNA encoding a dopamine $D_1$ receptor thereby reducing its translation.

This invention provides a method of determining the physiological effects of expressing varying levels of human dopamine $D_1$ receptors which comprises producing a transgenic nonhuman animal whose levels of human dopamine $D_1$ receptor expression are varied by use of an inducible promoter which regulates human dopamine $D_1$ receptor expression.

This invention also provides a method of determining the physiological effects of expressing varying levels of human dopamine $D_1$ receptors which comprises producing a panel of transgenic nonhuman animals each expressing a different amount of human dopamine $D_1$ receptor.

This invention provides a method for diagnosing in a subject a predisposition to a disorder associated with the expression of a specific human dopamine $D_1$ receptor allele which comprises a. isolating DNA from victims of the disorder, b. digesting the isolated DNA of step a with at least one restriction enzyme, c. electrophoretically separating the resulting DNA fragments on a sizing gel, d. contacting the resulting gel with a nucleic acid probe capable of specifically hybridizing to DNA encoding a human dopamine $D_1$ receptor and labelled with a detectable marker, e. detecting labelled bands which have hybridized to the DNA encoding a human dopamine $D_1$ receptor labelled with a detectable marker to create a band pattern specific to the DNA of victims of the disorder, f. preparing the subject's DNA by steps a–e to produce detectable labeled bands on a gel, and g. comparing the band pattern specific to the DNA of victims of the disorder of step e and the subject's DNA of step f to determine whether the patterns are the same or different and thereby to diagnose predisposition to the disorder if the patterns are the same. This method may also be used to diagnose a disorder associated with the expression of a specific human dopamine $D_1$ receptor allele.

This invention provides a method of preparing the isolated dopamine $D_1$ receptor which comprises inducing cells to express dopamine $D_1$ receptor, recovering the receptor from the resulting cells, and purifying the receptor so recovered.

This invention provides a method of preparing the isolated dopamine $D_1$ receptor which comprises inserting nucleic acid encoding dopamine $D_1$ receptor in a suitable vector, inserting the resulting vector in a suitable host cell, recovering the receptor produced by the resulting cell, and purifying the receptor so recovered.

BRIEF DESCRIPTION OF THE FIGURES

FIGS. 1A to 1E. Nucleotide and deduced amino acid sequence of the gene GL-30. (Also Seq. ID No. 1).

Numbers above the nucleotide sequence indicate nucleotide position. DNA sequence was determined by the chain termination method of Sanger, et al., on denatured doubled-stranded plasmid templates using the enzyme Sequenase. Deduced amino acid sequence (single letter code) of a long open reading frame is shown.

Figure 2A:
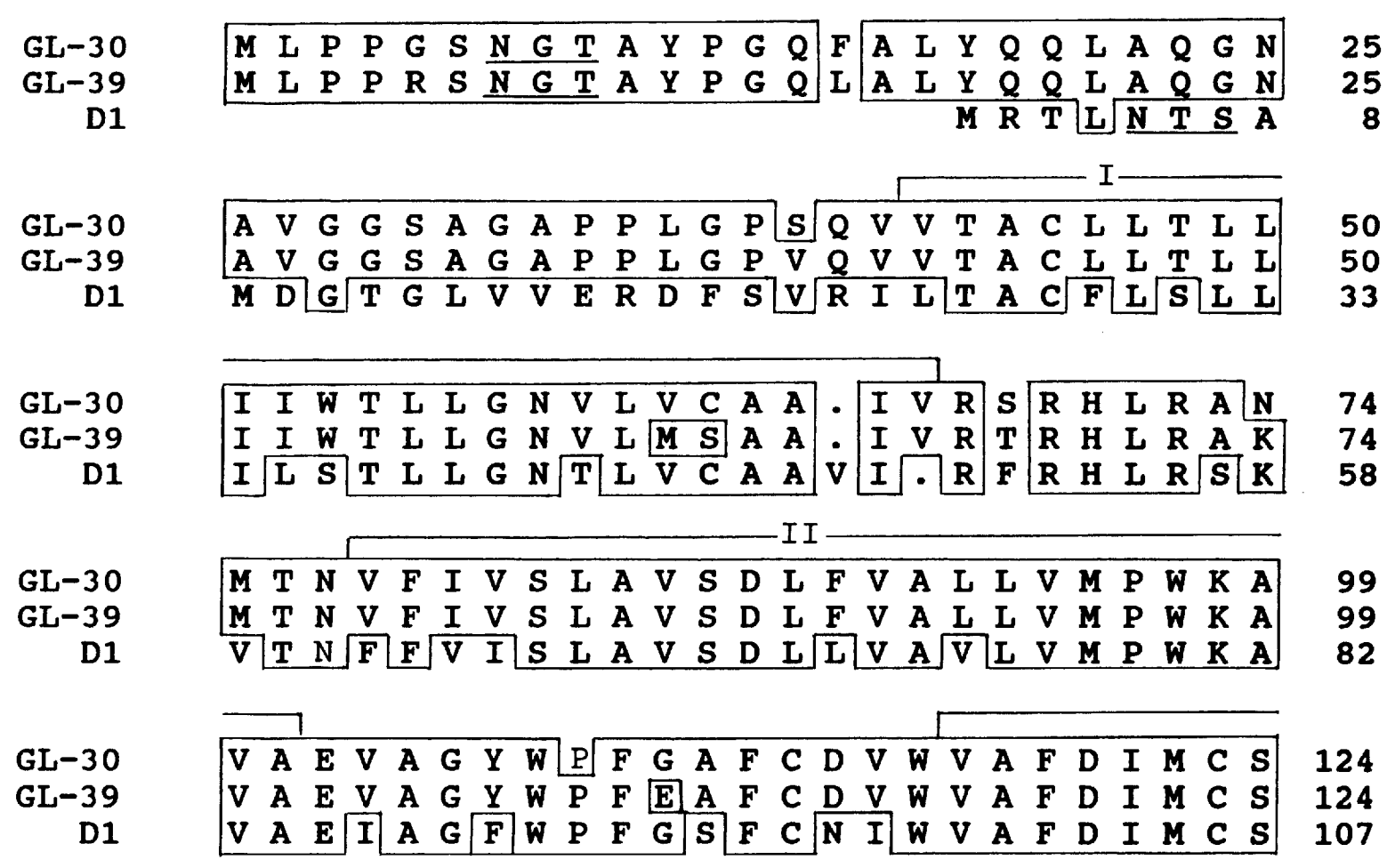

FIGS. 2A–2E. Comparison of the Dopamine $D_1$ (GL-30) receptor primary structure with other G-protein-coupled receptors. Amino acid sequences (single letter code) are aligned to optimize homology. GL-30 is the human dopamine receptor of this invention; GL-39 is the human dopamine pseudogene; and $D_1$ is the human dopamine $D_1$ receptor. (Also Seq. ID Nos. 2 to 4, respectively). It should be noted that a clone designated $D_5$ is the same sequence as that listed as GL-30. (Sunahara, et al. (April 1991) Nature, 350:614–619).

DETAILED DESCRIPTION OF THE INVENTION

As used herein, the dopamine receptor family is defined as the group of mammalian proteins that function as receptors for dopamine. A dopamine receptor subfamily is defined as a subset of proteins belonging to the dopamine receptor family which are encoded by genes which exhibit homology of 65% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Three human dopamine receptor subfamilies can be distinguished based on the information presently available. The dopamine $D_2$ receptor subfamily contains the dopamine $D_2$ receptor. There are currently two forms of this receptor which are generated by alternative splicing mechanisms (Toso, R. D., Sommer,B, Ewert, M, et al. (1989) EMBO 8:4025–4034; Chio, C. L. et al. (1990) Nature 343:266–269; Monsma, F. J. (1990) Nature 342:926–929). The dopamine $D_3$ receptor which exhibits significant homology to the $D_2$ receptor both in amino acid sequence and pharmacological properties (Sokoloff, P. et al. (1990) supra). The human dopamine $D_1$ receptor subfamily contains the human dopamine $D_1$ receptor gene GL-30 which is described herein, and the human dopamine $D_1$ receptor, not yet cloned or isolated, which represents the human counterpart of the rat $D_1$ clone (Sunahara R. K. (1990) Nature 347:80–83). Therefore, the term "human dopamine $D_1$ receptor" as used herein is defined as meaning a member of the dopamine $D_1$ receptor subfamily described above. Although this definition differs from the pharmacological definition used earlier, there is significant overlap between the present definition and the pharmacological definition. Members of the human dopamine $D_1$ receptor subfamily so described include the dopamine $D_1$ receptor clone known as GL-30 (which is also known as dopamine $D_{1\beta}$ receptor subtype) and any other receptors which have a 65% or greater transmembrane homology to the DNA and amino acid sequence shown in FIGS. 1A–1E (SEQ ID NO:1) according to the definition of "subfamily". This invention relates to the discovery of the first member of the human dopamine $D_1$ receptor subfamily.

This invention provides an isolated nucleic acid molecule such as a DNA molecule encoding a human dopamine $D_1$ receptor. Such a receptor is by definition a member of the dopamine $D_1$ receptor subfamily. Therefore, any receptor which meets the defining criteria given above is a human dopamine $D_1$ receptor. One means of isolating a human dopamine $D_1$ receptor is to probe a human genomic library with a natural or artificially designed DNA probe, using methods well known in the art. DNA probes derived from the human genes encoding dopamine $D_1$ receptor, for example clone GL-30 is a particularly useful probe for this purpose. DNA and cDNA molecules which encode human dopamine $D_1$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human dopamine $D_1$ receptor. Such molecules may have coding sequences substantially the same as the coding sequence shown in FIGS. 1A and 1B or may have coding sequences that are 65% or more homologous to the coding sequence shown in FIGS. 1A and 1B The DNA molecule of FIGS. 1A and 1B encodes a human dopamine $D_1$ receptor.

This invention further provides a cDNA molecule encoding a human dopamine $D_1$ receptor having a coding sequence substantially the same as the coding sequence shown in FIGS. 1A and 1B. This molecule is obtained by the means described above.

This invention also provides an isolated protein which is a human dopamine $D_1$ receptor. Examples of such proteins are an isolated protein having substantially the same amino acid sequence as the amino acid sequence shown in FIGS. 1A and 1B, which is a human dopamine $D_1$ receptor. One means for obtaining isolated dopamine $D_1$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human dopamine $D_1$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. An example of a plasmid is a plasmid comprising DNA having a coding sequence substantially the same as the coding sequence shown in FIGS. 1A and 1B and designated clone pdopD1-GL-30, deposited Jul. 10, 1990 with the American Type Culture Collection under ATCC Accession No. 40839.

This deposit was made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention also provides vectors comprising a DNA molecule encoding a human dopamine $D_1$ receptor adapted for expression in a bacterial cell, a yeast cell, or a mammalian cell which additionally comprise the regulatory elements necessary for expression of the DNA in the bacterial, yeast, or mammalian cells so located relative to the DNA encoding a human dopamine $D_1$ receptor as to permit expression thereof. DNA having coding sequences substantially the same as the coding sequence shown in FIGS. 1A–1E (SEQ ID NO:1) may usefully be inserted into the vectors to express human dopamine $D_1$ receptors. Regulatory elements required for expression include promoter sequences to bind RNA polymerase and transcription initiation sequences for ribosome binding. For example, a bacterial expression vector includes a promoter such as the lac promoter, and for transcription initiation, the Shine-Dalgarno sequence and the start codon ATG (Maniatis, et al., Molecular Cloning, Cold Spring Harbor Laboratory, 1982). Similarly, a eucaryotic expression vector includes a heterologous or homologous promoter for RNA polymerase II, a downstream polyadenylation signal, the start codon ATG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human dopamine $D_1$ receptor and the regulatory elements necessary for expression of the DNA in the bacterial, yeast, or mammalian cell so located relative to the DNA encoding a human dopamine $D_1$ receptor as to permit expression thereof. Some plasmids adapted for expression in a mammalian cell are PSVL (available from Pharmacia, Piscataway, N.J.) and pcEXV-3 (Miller J. and Germain R. N., J. Exp. Med. 164:1478 (1986)). Specific examples of such plasmids are a plasmid adapted for expression in a mammalian cell comprising cDNA having coding sequences substantially the same as the coding sequence shown in FIGS. 1A–1E (SEQ ID NO:1) and the regulatory elements necessary for expression of the DNA in the mammalian cell. Those skilled in the art will readily appreciate that numerous plasmids adapted for expression in a mammalian cell which comprise DNA encoding human dopamine $D_1$ receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

This invention provides a mammalian cell comprising a DNA molecule encoding a human dopamine $D_1$ receptor, such as a mammalian cell comprising a plasmid adapted for expression in a mammalian cell, which comprises a DNA molecule encoding a human dopamine $D_1$ receptor and the regulatory elements necessary for expression of the DNA in the mammalian cell so located relative to the DNA encoding a human dopamine $D_1$ receptor as to permit expression thereof. Numerous mammalian cells may be used as hosts, including the mouse fibroblast cell NIH3T3, CHO cells, HeLa cells, and Ltk-cells. Expression plasmids such as those described supra may be used to transfect mammalian cells by methods well known in the art such as calcium phosphate precipitation, or DNA encoding these dopamine $D_1$ receptors may be otherwise introduced into mammalian cells, e.g., by microinjection, to obtain mammalian cells which comprise DNA, e.g., cDNA or a plasmid, encoding a human dopamine $D_1$ receptor.

This invention provides a method for determining whether a ligand not known to be capable of binding to a human dopamine $D_1$ receptor can bind to a human dopamine $D_1$ receptor which comprises contacting a mammalian cell comprising a DNA molecule encoding a human dopamine $D_1$ receptor with the ligand under conditions permitting binding of ligands known to bind to the dopamine $D_1$ receptor, detecting the presence of any of the ligand bound to the dopamine $D_1$ receptor, and thereby determining whether the ligand binds to the dopamine $D_1$ receptor. Methods for performing this technique are well known in the art. The DNA in the cell may have a coding sequence substantially the same as the coding sequence shown in FIGS. 1A and 1B. Preferably, the mammalian cell is nonneuronal in origin. An example of a nonneuronal mammalian cell is an Ltk-cell. (Stable cell lines can be produced by cotransfection of an expression plasmid such as PSVL or pcEXV, into which the DNA of FIGS. 1A–1E (SEQ ID NO:1) has been subcloned, with a plasmid containing the bacterial gene aminoglycoside phosphotransferase into Ltk- cells (American Type Culture Collection, Rockville, Md., Cell Line CCL 1,3) using the calcium phosphate technique (protocol & kit obtained from Specialty Media, Inc. Lavallette, N.J.). Clones expressing aminoglycoside transferase can then be selected by the addition of 1 mg/ml G418 (Gibco Laboratories, Grand Island, N.Y.) to the culture medium. The preferred method for determining whether a ligand is capable of binding to the human dopamine $D_1$ receptors comprises contacting a transfected nonneuronal mammalian cell (i.e. a cell that does not naturally express any type of dopamine or G-protein coupled receptor, thus will only express such a receptor if it is transfected into the cell) expressing a dopamine $D_1$ receptor on its surface, or contacting a membrane preparation derived from such a transfected cell, with the ligand under conditions which are known to prevail, and thus to be associated with, in vivo binding of the ligands to a dopamine $D_1$ receptor, detecting the presence of any of the ligand being tested bound to the dopamine $D_1$ receptor on the surface of the cell, and thereby determining whether the ligand binds to the dopamine $D_1$ receptor. (Methods for so doing are well known in the art, for example a tritiated ligand can be used as a radioligand to detect binding to membrane fractions isolated from either transiently or stably transfected cell lines which express human dopamine $D_1$ receptor. Tritiated SCH-23390 (71.3 Ci/mMol; Dupont-NEN), which is known in the art to bind with high affinity to the dopamine $D_1$ receptor, is used as a radioligand to detect the expression of the dopamine $D_1$ gene product in membrane fractions isolated from either transiently or stably transfected cell lines. The incubation buffer contains 50 mM Tris-HCl pH 7.4; 120 mM NaCl, 5 mM KCl, 1 mM $MgCl_2$; 2 mM $CaCl_2$; 0.1% ascorbic acid; and 1 $\mu$M pargyline, and incubation is initiated by adding cell membranes 10–50 $\mu$g/well to a 96 well microtiter plate containing tritiated SCH-23390 (final concentration 5 nM) in a final volume of 250 $\mu$l. After incubating 20 minutes at 37° C. in the dark, incubation is terminated by rapid filtration with a Brandel Model 48R Cell Harvester (Brandel, Gaithersville, Md.). The tritiated SCH-23390 that has bound to the dopamine receptors on the cell membrane is retained on the filters, which are placed in scintillation vials with a scintillation fluid (such as Ready Safe, Beckman Instruments, Fullerton, Calif.) and counted in a scintillation counter (such as a Beckman LS5000 TA). Specific binding of tritiated SCH-23390 is determined by defining nonspecific binding with $10^{-6}$M cis(−) flupentixol. To determine whether a ligand binds to dopamine $D_1$ receptor, the ligand can be tritiated by methods well known in the art, and the technique described above for SCH-23390 binding performed. But a more efficient method is to perform competition studies. The method described above is performed, however in addition to tritiated SCH-23390, a different unlabeled ligand is added to each well of the incubation except control wells. Ligands are initially screened at a concentration of 1–10 times their reported Ki values for dopamine $D_1$ receptor binding by liquid scintillation spectroscopy in a Beckman LS5000 TA scintillation counter using Ready Safe liquid scintillation cocktail (Beckman Instruments, Fullerton, Calif.) at an efficiency of 50–55% Whichever ligand reduces the counts of radioactivity over the counts of tritiated SCH-23390 alone has competitively reduced binding of the tritiated SCH-23390 by itself binding to the dopamine receptor). This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human dopamine $D_1$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human dopamine $D_1$ receptor. The transfection system is also useful for determining the affinity and efficacy of known drugs at the human dopamine $D_1$ receptor sites.

This invention also provides a ligand detected by the method described supra.

This invention also provides a method of screening drugs to identify drugs which specifically interact with, and bind to, the human dopamine $D_1$ receptor on the surface of a cell which comprises contacting a mammalian cell comprising a DNA molecule encoding a human dopamine $D_1$ receptor on the surface of a cell with a plurality of drugs, determining those drugs which bind to the mammalian cell, and thereby identifying drugs which specifically interact with, and bind to, the human dopamine $D_1$ receptor. The DNA in the cell may have a coding sequence substantially the same as the coding sequence shown in FIGS. 1A–1E (SEQ ID NO:1). Preferably, the mammalian cell is nonneuronal in origin, such as an Ltk-cell. Drug candidates are identified by choosing chemical compounds which bind with high affinity to the expressed dopamine $D_1$ receptor protein in transfected cells, using radioligand binding methods well known in the art and described supra. Drug candidates are also screened for selectivity by identifying compounds which bind with high affinity to one particular dopamine receptor but do not bind with high affinity to any other dopamine receptor subtype or to any other known receptor site. Because selective, high affinity compounds interact primarily with the target dopamine $D_1$ receptor site after administration to the patient, the chances of producing a drug with unwanted side effects are minimized by this approach. This invention provides a pharmaceutical composition comprising a drug identified by the method described above and a pharmaceutically acceptable carrier. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human dopamine $D_1$ receptor, for example with a coding sequence included within the sequence shown in FIGS. 1A–1E (SEQ ID NO:1). Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human dopamine $D_1$ receptors is useful as a diagnostic test for any disease process in which levels of expression of the corresponding dopamine $D_1$ receptor is altered. DNA probe molecules are produced by insertion of a DNA molecule which encodes human dopamine $D_1$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A and 1B. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a human dopamine $D_1$ receptor of are useful as probes for these genes, for their associated mRNA, or for the isolation of related genes by homology screening of genomic or cDNA libraries, or by the use of amplification techniques such as the polymerase chain reaction.

This invention also provides a method of detecting expression of a dopamine $D_1$ receptor on the surface of a cell by detecting the presence of mRNA coding for a dopamine $D_1$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human dopamine $D_1$ receptor under hybridizing conditions, detecting the presence of mRNA hybridized to the probe, and thereby detecting the expression of the dopamine $D_1$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human dopamine $D_1$ receptor so as to prevent translation of the mRNA molecule. The antisense oligonucleotide may have a sequence capable of binding specifically with any sequences of the DNA molecule whose sequence is shown in FIGS. 1A and 1B. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human dopamine $D_1$ receptor by passing through a cell membrane and binding specifically with mRNA encoding a human dopamine $D_1$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIGS. 1A and 1B may be used as the oligonucleotides of the pharmaceutical composition.

This invention also provides a method of treating abnormalities which are alleviated by reduction of expression of a dopamine $D_1$ receptor which comprises administering to a subject an amount of the pharmaceutical composition described above effective to reduce expression of the dopamine $D_1$ receptor by the subject. This invention further provides a method of treating an abnormal condition related to dopamine $D_1$ receptor activity which comprises administering to a subject an amount of the pharmaceutical composition described above effective to reduce expression of the dopamine $D_1$ receptor by the subject. Several examples of such abnormal conditions are dementia, Parkinson's disease, abnormal cognitive functioning such as schizophrenia, tardive dyskinesia, renal failure, and failure of vascular control, abnormal circadian rhythms, and abnormal visual activity.

Antisense oligonucleotide drugs inhibit translation of mRNA encoding these receptors. Synthetic oligonucleotides, or other antisense chemical structures are designed to bind to mRNA encoding the dopamine $D_1$ receptor and inhibit translation of mRNA and are useful as drugs to inhibit expression of dopamine $D_1$ receptor genes in patients. This invention provides a means to therapeutically alter levels of expression of human dopamine $D_1$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 1A and 1B of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequences shown in FIGS. 1A and 1B, by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent when it is administered to a patient by injection, or when the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of dopamine $D_1$ receptor.

This invention provides an antibody directed to the human dopamine $D_1$ receptor, for example a monoclonal antibody directed to an epitope of a human dopamine $D_1$ receptor present on the surface of a cell and having an amino acid sequence substantially the same as an amino acid sequence for a cell surface epitope of the human dopamine $D_1$ receptor included in the amino acid sequence shown in FIGS. 1A and 1B. Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A and 1B will bind to a surface epitope of a human dopamine $D_1$ receptor, as described. Antibodies directed to human dopamine $D_1$ receptor may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as SR3T3 cells or Ltk-cells may be used as immunogens to raise such an antibody. Alternatively, synthetic peptides may be prepared using commercially available machines and the amino acid sequences shown in FIGS. 1A and 1B. As a still further alternative, DNA, such as a cDNA or a fragment thereof, may be cloned and expressed and the resulting polypeptide recovered and used as an immunogen. These antibodies are useful to detect the presence of human dopamine $D_1$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human dopamine $D_1$ receptor effective to block binding of naturally occurring ligands to the dopamine $D_1$ receptor, and a pharmaceutically acceptable carrier. A monoclonal antibody directed to an epitope of a human dopamine $D_1$ receptor present on the surface of a cell and having an amino acid sequence substantially the same as an amino acid sequence for a cell surface epitope of the human dopamine $D_1$ receptor included in the amino acid sequence shown in FIGS. 1A and 1B are useful for this purpose.

This invention also provides a method of treating abnormalities which are alleviated by reduction of expression of a human dopamine $D_1$ receptor which comprises administering to a subject an amount of the pharmaceutical composition described above effective to block binding of naturally occurring ligands to the dopamine $D_1$ receptor and thereby alleviate abnormalities resulting from overexpression of a human dopamine $D_1$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of dopamine $D_1$ receptor activity which comprises administering to a subject an amount of the pharmaceutical composition described above effective to block binding of naturally occurring ligands to the dopamine $D_1$ receptor and thereby alleviate the abnormal condition. Several examples of such abnormal conditions are dementia, Parkinson's disease, abnormal cognitive functioning such as schizophrenia, tardive dyskinesia, renal failure, and failure of vascular control, abnormal circadian rhythms, and abnormal visual activity.

This invention provides a method of detecting the presence of a human dopamine $D_1$ receptor on the surface of a cell which comprises contacting the cell with an antibody directed to the human dopamine $D_1$ receptor, under conditions permitting binding of the antibody to the receptor, detecting the presence of the antibody bound to the cell, and thereby the presence of the human dopamine $D_1$ receptor on the surface of the cell. Such a method is useful for determining whether a given cell is defective in expression of dopamine $D_1$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human dopamine $D_1$ receptor. This invention also provides a transgenic nonhuman mammal expressing DNA encoding a human dopamine $D_1$ receptor so mutated as to be incapable of normal receptor activity, and not expressing native dopamine $D_1$ receptor. This invention also provides a transgenic nonhuman mammal whose genome comprises antisense DNA complementary to DNA encoding a human dopamine $D_1$ receptor so placed as to be transcribed into antisense mRNA which is complementary to mRNA encoding a dopamine $D_1$ receptor and which hybridizes to mRNA encoding a dopamine $D_1$ receptor thereby r educing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIGS. 1A and 1B. An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of human dopamine $D_1$ receptors are produced by creating transgenic animals in which the expression of a dopamine $D_1$ receptor is either increased or decreased, or the amino acid sequence of the expressed dopamine $D_1$ receptor protein is altered, by a variety of techniques. Examples of these techniques include: 1) Insertion of normal or mutant versions of DNA encoding a human dopamine $D_1$ receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)); 2) Homologous recombination (Capecchi M. R. Science 244:1288–1292 (1989); Zimmer, A. and Gruss, P. Nature 338:150–153 (1989)) of mutant or normal, human or animal versions of the gene with the native gene locus in transgenic animals to alter the regulation of expression or the structure of the dopamine $D_1$ receptor. The technique of homologous recombination is well known in the art. This technique replaces the native gene with the inserted gene and so is useful for producing an animal that cannot express native receptor but does express, for example, an inserted mutant receptor, which has replaced the native receptor in the animal's genome by recombination, resulting in underexpression of the receptor (in more detail, mutually homologous regions of the insert DNA and genomic DNA pair with each other, resulting in the replacement of the homologous regions of genomic DNA and regions between the homologous regions with the insert). Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human dopamine $D_1$ receptor is purified from a vector (such as plasmid pdopD1-GL-30 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only as an example. Since the normal action of receptor-specific drugs is to activate or to inhibit the receptor, the transgenic animal model systems described above are useful for testing the biological activity of potential drugs directed against the dopamine $D_1$ receptor even before such drugs become available. These animal model systems are useful for predicting or evaluating possible therapeutic applications of drugs which activate or inhibit the dopamine $D_1$ receptor by inducing or inhibiting expression of the native or transgene and thus increasing or decreasing expression of normal or mutant dopamine $D_1$ receptors in the living animal. Thus, a model system is produced in which the biological activity of a potential drug directed against the dopamine $D_1$ receptor can be evaluated before the actual development of such a drug. The transgenic animals which over or under produce the dopamine $D_1$ receptor indicate by their physiological state whether over or under production of the dopamine $D_1$ receptor is therapeutically useful. The transgenic model system is therefore useful to evaluate potential drug action. For example, it is well known in the art that a drug such as an antidepressant acts by blocking neurotransmitter uptake, and thereby increases the amount of neurotransmitter in the synaptic cleft. The physiological result of this action is to stimulate reduced production of receptor by the affected cells, leading eventually to underexpression. Therefore, an animal which is engineered to underexpress receptor is useful as a test system to investigate whether the action of a drug which results in underexpression is in fact therapeutic. Again, for example, if overexpression is found to lead to abnormalities, then a drug which can down-regulate or act as an antagonist to dopamine $D_1$ receptor is indicated as worth developing. If a promising therapeutic application is uncovered by these animal model systems, activation or inhibition of the dopamine $D_1$ receptor can be achieved therapeutically either by producing agonist or antagonist drugs directed against the dopamine $D_1$ receptor, or indeed by any method which increases or decreases the expression of the dopamine $D_1$ receptor.

This invention provides a method of determining the physiological effects of expressing varying levels of human dopamine $D_1$ receptors which comprises producing a transgenic nonhuman animal whose levels of human dopamine $D_1$ receptor expression are varied by use of an inducible promoter which regulates human dopamine $D_1$ receptor expression. This invention also provides a method of determining the physiological effects of expressing varying levels of human dopamine $D_1$ receptors which comprises producing a panel of transgenic nonhuman animals each expressing a different amount of human dopamine $D_1$ receptor. Such animals may be produced by introducing different amounts of DNA encoding a human dopamine $D_1$ receptor into the oocytes from which the transgenic animals are developed.

This invention also provides a method for identifying a substance capable of alleviating abnormalities resulting from overexpression of a human dopamine $D_1$ receptor comprising administering the substance to a transgenic nonhuman mammal expressing at least one artificially introduced DNA molecule encoding a human dopamine $D_1$ receptor and determining whether the substance alleviates the physical and behavioral abnormalities displayed by the transgenic nonhuman mammal as a result of overexpression of a human dopamine $D_1$ receptor. Examples of DNA molecules are DNA or cDNA molecules having a coding sequence substantially the same as the coding sequence shown in FIGS. 1A and 1B.

This invention provides a pharmaceutical composition comprising an amount of the substance described supra effective to alleviate the abnormalities resulting from overexpression of dopamine $D_1$ receptor and a pharmaceutically acceptable carrier.

This invention further provides a method for treating the abnormalities resulting from overexpression of a human dopamine $D_1$ receptor which comprises administering to a subject an amount of the pharmaceutical composition described above effective to alleviate the abnormalities resulting from overexpression of a human dopamine $D_1$ receptor.

This invention provides a method for identifying a substance capable of alleviating the abnormalities resulting from underexpression of a human dopamine $D_1$ receptor comprising administering the substance to the transgenic nonhuman mammal described above which expresses only nonfunctional human dopamine $D_1$ receptor and determining whether the substance alleviates the physical and behavioral abnormalities displayed by the transgenic nonhuman mammal as a result of underexpression of a human dopamine $D_1$ receptor.

This invention also provides a pharmaceutical composition comprising an amount of a substance effective to alleviate abnormalities resulting from underexpression of dopamine $D_1$ receptor and a pharmaceutically acceptable carrier.

This invention further provides a method for treating the abnormalities resulting from underexpression of a human dopamine $D_1$ receptor which comprises administering to a subject an amount of the pharmaceutical composition described above effective to alleviate the abnormalities resulting from underexpression of a human dopamine $D_1$ receptor.

This invention provides a method for diagnosing in a subject a predisposition to a disorder associated with the expression of a specific human dopamine $D_1$ receptor allele which comprises: a. isolating DNA from victims of the disorder, b. digesting the isolated DNA of step a with at least one restriction enzyme, c. electrophoretically separating the resulting DNA fragments on a sizing gel, d. contacting the resulting gel with a nucleic acid probe capable of specifically hybridizing to DNA encoding a human dopamine $D_1$ receptor and labelled with a detectable marker, e. detecting labelled bands which have hybridized to the DNA encoding a human dopamine $D_1$ receptor labelled with a detectable marker to create a band pattern specific to the DNA of victims of the disorder, f. preparing the subject's DNA by steps a–e to produce detectable labeled bands on a gel, and g. comparing the band pattern specific to the DNA of victims of the disorder of step e and the subject's DNA of step f to determine whether the patterns are the same or different and thereby to diagnose predisposition to the disorder if the patterns are the same. This method may also be used to diagnose a disorder associated with the expression of a specific human dopamine $D_1$ receptor allele. This method makes use of restriction fragment length polymorphisms in the gene of interest, which may itself encode an abnormal phenotype, or may encode or predispose to an abnormal phenotype in one of its allelic forms, or may encode an abnormal phenotype when present in mutant form. A DNA probe is a useful genetic probe for an allelic abnormality. An allele of a gene will have a specific restriction fragment pattern when its isolated DNA is digested with a single restriction enzyme or panel of restriction enzymes, because of polymorphisms in the areas of the gene which have nucleotide sequences that form sites for restriction enzymes. For example, the gene may have the sequence AATTC which forms the site for the enzyme EcoRI. Its allele may have in the same area the sequence AAATC. When the isolated DNA comprising the gene and its allele are digested with EcoRI by methods well known in the art, the gene will be cut at the site described and this cut will create a fragment of a length determined by the location of the next EcoRI site (assuming this is a single-enzyme digest). The allele will not be cut at this site, therefore the fragment generated by the digest will be longer. When the DNA digest is run on an agarose or polyacrylamide sizing gel and hybridized with the detectably labelled DNA probe for the gene, the detectable band visualized on the gel will correspond to the length of the restriction fragments produced. If the fragment is the "long" fragment, then this result indicates that the allele is carried by the DNA digested. If the presence of the allelic form of the gene is associated with a predisposition to a phenotypic abnormality, then the predictive power of such an analysis is important. If the abnormality already exists, then this test is useful for diagnosis and differential diagnosis. An allele is given only as an example. This method may be used to detect mutations and polymorphisms of a gene of interest, or the gene itself. Methods for isolating DNA (from a source such as a blood or tissue sample, for example) are well known in the art. Methods of visualizing a labeled nucleic acid probe hybridized to a gel are also well known in the art. For example, the DNA on a gel is denatured with base, incubated with a radioactively labeled probe, and a filter (usually nitrocellulose) is placed over the gel, transferring the fragments on the gel to the filter. A piece of film is laid over the filter. The fragments which have hybridized to the probe will expose the film and leave a band marking their positions in the gel.

This invention provides a method of preparing the isolated dopamine $D_1$ receptor which comprises inducing cells to express dopamine $D_1$ receptor, recovering the receptor from the resulting cells, and purifying the receptor so recovered. An example of an isolated dopamine $D_1$ receptor is an isolated protein having substantially the same amino acid sequence as the amino acid sequence shown in FIG. 1. For example, cells can be induced to express receptors by exposure to substances such as hormones. The cells can then be homogenized and the receptor isolated from the homogenate using an affinity column comprising, for example, dopamine, or antibody to the dopamine $D_1$ receptor, or another substance which is known to bind to the receptor. The resulting fractions can then be purified by contacting them with an ion exchange column, and determining which fraction contains receptor activity or binds anti-receptor antibodies. These methods are provided as examples, and do not exclude the use of other methods known in the art for isolating proteins.

This invention provides a method of preparing the isolated dopamine $D_1$ receptor which comprises inserting nucleic acid encoding dopamine $D_1$ receptor in a suitable vector, inserting the resulting vector in a suitable host cell, recovering the receptor produced by the resulting cell, and purifying the receptor so recovered. An example of an isolated dopamine $D_1$ receptor is an isolated protein having substantially the same amino acid sequence as the amino acid sequence shown in FIGS. 1A and 1B. This method for preparing dopamine $D_1$ receptor uses recombinant DNA technology methods well known in the art. For example, isolated nucleic acid encoding dopamine $D_1$ receptor is inserted in a suitable vector, such as an expression vector. A suitable host cell, such as a bacterial cell, or a eucaryotic cell such as a yeast cell, is transfected with the vector. The dopamine $D_1$ receptor is isolated from the culture medium by affinity purification or by chromatography or by other methods well known in the art.

Applicants have identified individual receptor subtype proteins and have described methods for the identification of pharmacological compounds for therapeutic treatments. Pharmacological compounds which are directed against specific receptor subtypes provide effective new therapies with minimal side effects.

Disturbances of dopaminergic neurotransmission have been associated with a wide range of neurological, endocrine, and psychiatric disorders, including Parkinson's disease, tardive dyskinesia, and schizophrenia. The neuroleptics, which have highest affinity for $D_2$ receptors have major side effects involving movement disorders and hypersecretion of prolactin. Drugs used in the treatment of Parkinson's disease cause nausea, vomiting, choreiform movements, psychiatric disturbances including hallucinations, and cardiovascular disorders. Some of these effects are likely to be due to actions on $D_1$ receptors or to a disruption in the balance of activity between the $D_1$ and $D_2$ systems (Abbott, A., 1990; TIPS 11: 49–51). In fact some therapeutic benefit of $D_1$ antagonists which lack $D_2$ activity may be obtained. (Hess, E. J. and Creese, I., in Neurobiology of Central $D_1$ Receptors, eds, G. R. Breese and I. Creese pp. 53–72) Drugs selectively targeted to $D_1$ receptor may be useful neuroleptics without resulting in the tardive dyskinesia thought to be the result of $D_2$ receptor up-regulation caused by chronic $D_2$ antagonism (Hess, E. J. and Creese, I., in Neurobiology of Central $D_1$ Receptors, eds, G. R. Breese and I. Creese pp. 53–72). Furthermore, evidence provided by the anatomical distribution of $D_1$ receptors in the brain suggest roles for $D_1$ selective drugs in cognitive function, control of visual activity and circadian rhythms (Dawson, T., Gelhert, D., McCabe, R., Barnett, A. , and Wamsley, J. 1986; J. Neurosci. 6:2352–2365) Finally, the distribution of $D_1$ receptors on the renal vasculature indicates potential therapeutic value of selective $D_1$ agents to ameliorate renal failure secondary to heart attack (Missale, C., Castelleti, L., Memo, M., Carruba, M., and Spano, P. 1988; J. Cardiovascular Research 11: 643–650). Its general action on vascular smooth muscle in other portions of the vascular tree may indicate a general role in cardiovascular control (Missale, as above; Hilditch, A. and Drew, G. M. 1985, TIPS 6:396–400).

In animal models, $D_1$-selective benzazepines induce intense grooming (Molloy, A. G. and Waddington, J. L. (1987), Psychopharmacology (Berlin) 92, 164–168), inhibit spontaneous locomotion (Hjorth, S. and Carlsson, A. (1988), J. Neural Transm. 72, 83–97), and generally seem to facilitate D2 receptor activities (Waddington, J. L. (1986), Biochem. Pharmacol. 35, 3661–3667; Hjorth, S. and Carlsson, A. (1988), J. Neural Transm. 72, 83–97). These actions produce therapeutic applications in enhancing Parkinson's disease or antipsychotic therapies with existing $D_2$ antagonists (Waddington, J. L. (1986), Biochem. Pharmacol. 35, 3661–3667). In human peripheral arteries, $D_{A1}$ receptors mediate vasodilation (Toda, N., Okunishi, H., and Okamura, T. (1989), Arch Int. Pharmacodyn. Ther. 297, 86–97). Clinical trials with the selective $D_{A1}$ receptor agonist, fenoldopam, have revealed a potent renal vasodilatory action that could provide an attractive alternative therapy for treating hypertensive and congestive heart failure patients (Carey, R. A. and Jacob, L. (1989), J. Clin Pharmacol. 29, 207–211). Development of more selective $D_1$ agonists and antagonists will expand existing $D_1$ therapeutic applications and suggest new ones.

This invention identifies for the first time a new human receptor protein, the dopamine $D_1$ receptor, its amino acid sequences, and its human gene, clone GL-30. The first isolated human cDNA and genomic clone encoding dopamine $D_1$ receptor are identified and characterized herein. The information and experimental tools provided by this discovery will be useful to generate new therapeutic agents, and new therapeutic or diagnostic assays for the new receptor protein, associated mRNA molecules, or associated genomic DNA.

The invention will be better understood by reference to the Experimental Details which follow, but those skilled in the art will readily appreciate that the specific experiments detailed are only illustrative of the invention as described more fully in the claims which follow thereafter.

Experimental Details:

Homology Cloning. A human spleen genomic library, provided by Dr. Jeffrey V. Ravetch (Sloan-Kettering Institute, New York, N.Y.), was screened using the 1.6-kilobase (kb) Xba1-BamHI fragment from the human 5-hydroxytryptamine (5-$HT_{1A}$) receptor gene as a probe. The probe was labeled with $^{32}P$ by the method of random priming. Hybridization was performed at 40° C. in a solution containing 25% formamide, 10% dextran sulfate, 5× SSC (1× SSC is 0.15M sodium chloride, 0.015M sodium citrate) 1× Denhardt's (0.02% polyvinyl-pyrrolidone, 0.02% Ficoll, and 0.02% bovine serum albumin), and 200 µg/ml. of sonicated salmon sperm DNA. The filters were washed at 40° C. in 0.1× SSC containing 0.1% sodium-dodecyl-sulfate (SDS) and exposed at −70° C. to Kodak XAR film in the presence of an intensifying screen. Lambda phage hybridizing to the probe were plaque purified and DNA was prepared for Southern blot analysis (Maniatis et al., Molecular Cloning, Cold Spring Harbor, 1982; E. Southern, J. Mol. Biol. 98:503, 1975). For subcloning and further southern blot analysis DNA was inserted into pUC18 (Pharmacia, Piscataway, N.J.).

DNA Sequencing

Nucleotide sequence analysis was done by the Sanger dideoxy nucleotide chain-termination method (S. Sanger, et al., Proc. Natl. Acad. Sci., 74: 5463–5467, 1977) on denatured double-stranded plasmid templates (Chen and Seeburg, DNA 4: 165, 1985) using Sequenase (U.S. Biochemical Corp., Cleveland, Ohio).

Receptor Expression in Transfected Mammalian Cells

To confirm the functional identity of the newly isolated gene clone GL-30 was expressed in cultured cell lines. The entire coding region of GL-30, including 113 base pairs of 5' untranslated sequence, and approximately 1.3 kb of 3' untranslated sequence, was cloned into the eucaryotic expression vector pcEXV-3 (Miller, J. and Germain, R. N. (1986), J. Exp. Med. 164: 1478–89). The resulting plasmid was transiently transfected into Cos-7 cells using the DEAE-dextran procedure (Cullen, Methods in Enz., 152: 684–704, 1987).

Measurement of cAMP Formation

The transiently transfected plates were incubated in Dulbecco's modified Eagle's medium (DMEM, Specialty Media, Lavallette, N.J.), 5 mM theophylline, 10 mM Hepes, 10 µM pargyline, 10 µM propanolol, and/or 10 µM SCH-23390 for 20 minutes at 37° C., 5% $CO_2$. In these experiments, the β-adrenergic antagonist propanolol was included in the assay to preclude stimulation of the endogenous Cos-7 cell β-adrenergic receptor by dopamine. Dopamine or SKF-38393 was then added to a final concentration of 1 µM and incubated for an additional 10 minutes at 37° C., 5% $CO_2$. The media was aspirated and the reaction stopped by the addition of 100 mM HCl. The plates were stored at 4° C. for 15 minutes, centrifuged for 5 minutes, 500×g to pellet cellular debris, and the supernatant aliquotted and stored at −20° C. prior to assessment of cAMP formation by radioimmunoassay (cAMP Radioimmunoassay Kit, Advanced Magnetics, Cambridge, Mass.).

Membrane Preparation

Membranes were harvested from transfected Cos-7 cells which were grown to 100% confluency. The cells were washed twice with phosphate-buffered saline (PBS), scraped into 5 ml of ice-cold PBS and centrifuged at 200×g for 5 minutes at 4° C. The pellet was resuspended in 2.5 ml ice-cold Tris buffer (20 mM Tris HCl, pH 7.4 at 23° C., 5 mM EDTA), hand homogenized in a Wheaton tissue grinder and the lysate centrifuged at 200×g for 5 minutes at 4° C. to pellet large fragments. The supernatant was then centrifuged at 40,000×g for 20 minutes at 4° C. The membranes were washed once and resuspended in the homogenization buffer. All preparations were kept on ice and assays were run on the day on which the membranes were collected. Protein concentration was determined by the method of Bradford (Anal. Biochem. 72: 248–54 (1976)) using bovine serum albumin as standard.

Radioligand Binding Studies

Binding assays were performed in triplicate in total volume of 250 $\mu$l containing buffer (50 mM Tris HCl, 10 mM MgSO$_4$, 1.5 mM EDTA, 150 mM NaCl, 0.1% ascorbate, 10 $\mu$M pargyline, pH 7.4 at 4° C.), [$^3$H]SCH-23390 (87 Ci/mmol; DuPont-NEN, Wilmington, Del.) and tested drugs. In competition binding experiments, 0.5–0.6 nM [$^3$H]SCH-23390 was inhibited by various concentrations of unlabeled drugs. Binding was initiated by the addition of membrane preparation (10–20 $\mu$g protein) and carried out at 22° C. for 90 minutes. Specific binding was 95% of total binding at 0.5 nM [$^3$H]SCH-23390. For saturation experiments, membranes were incubated with [$^3$H]SCH-23390 over the concentration range of 0.01–6.5 nM. Incubations were allowed to proceed for 150 minutes at 22° C. to ensure that equilibrium was achieved at the lowest concentrations of radioligand. Nonspecific binding was defined in the presence of 10 $\mu$M (+) butaclamol. The reaction was terminated by rapid filtration through Whatman GF/B glass fiber filters (presoaked with 0.5% polyethyleneamine, pH 7.4), using a Brandel 48R cell harvester (Brandel; Gaithersburg, Md.). Filters were washed for 5 seconds with iced buffer to reduce nonspecific binding. Dried filters were transferred to scintillation vials and radioactivity was determined by liquid scintillation counting (Beckman LS 1701; Beckman Instruments, Fullerton, Calif.). Ready Safe (Beckman) was used as the scintillant and the counting efficiency was 50%. Analysis of saturation and competition data were performed by computer-assisted nonlinear regression (DeLean et al., 1978; programs Accucomp and Accufit; Lundon Software, Chagrin Falls, Ohio). IC$_{50}$ values were converted to K$_i$ values by the Cheng-Prusoff equation (Cheng and Prusoff, 1973).

Experimental Results:

Isolation of a Genomic Clone Encoding a Dopamine D$_1$ Receptor.

We have screened human genomic spleen and human genomic placental libraries with the 1.6 kb Xba-1-Bam-H1 restriction fragment derived from the gene for the 5-HT$_{1A}$ receptor. A total of 59 clones were isolated and were characterized by restriction endonuclease mapping. One clone (designated GL-30) was isolated as an approximately 4.0 kb EcoRI-Bgl-II fragment was subcloned into pUC-18 and subject to sequence analysis.

Predicted Structure of the Receptor Encoded by GL-30

DNA sequence information obtained from GL-30 is shown in FIGS. 1A and 1B. An open reading frame encoding a protein of 477 amino acids in length, having a relative molecular mass (M$_r$) of approximately 53 kD. A comparison of this protein sequence with previously characterized neurotransmitter receptors indicates that clone GL-30 is a new member of a family of molecules which span the lipid bilayer seven times and couple to guanine nucleotide regulatory proteins (the G protein-coupled receptor family). A variety of structural features which are invariant in the G-protein coupled receptor family, including the aspartic acid residues of transmembrane regions II and III, the DRY sequence at the lend of transmembrane region III, and the conserved proline residues of transmembrane regions IV, V, VI and VII were present in clone GL-30. Both the amino terminus and the extracellular loop 2 (located between transmembrane domains IV and V) of GL-30, contain consensus sites for N-linked glycosylation. In addition, this extracellular loop contains 45 amino acids (as compared to 31 amino acids in the comparable region of the dopamine D$_1$ receptor) and represents the longest extracellular loop 2 of all the known G-protein coupled receptors. While the carboxy-terminal tails of the dopamine D$_1$ receptor and GL-30 are approximately the same size, their amino acid sequences are only 41% identical. When compared to all the known G protein-coupled receptors, the greatest homology was found to be with the dopamine D$_1$ receptor. While the overall homology between GL-30 and the human dopamine D$_1$ receptor was 62%, the homology within the seven membrane spanning domains was 83% FIGS. 2A–2E (SEQ ID NO: 2–4).

Discussion

Applicants have cloned and characterized a DNA molecule encoding a new dopamine D$_1$ receptor by low stringency hybridization to the serotonin 5-HT$_{1A}$ receptor. Although the amino acid sequence homology of clone GL-30 to the 5-HT$_{1A}$ receptor was relatively low (47% transmembrane region identity), comparison of this sequence to previously cloned dopamine receptors showed that the closest relationship was to the human dopamine D$_1$ receptor (83% identity in the transmembrane domains). In contrast, the transmembrane homology to either the dopamine D$_2$ or dopamine D$_3$ receptors was only 53% and 48%, respectively.

Clone GL-30 was expressed in Cos-7 cells in order to characterize the pharmacological binding properties of the expressed receptor protein. [$^3$H]SCH-23390, a highly selective D$_1$ antagonist in the rat (Billard, W. et al. (1984) Life Sci. 35: 1885–93), non-human primate (Madras, B. K. et al. (1988) J. Neurochem. 51: 934–43) and human brain (DeKeyser, J. et al. (1988) Brain Res. 443: 77–84; Raisman, R. et al. (1985) Eur. J. Pharmacol. 113: 467–68) binds to this receptor with an apparent dissociation constant (K$_d$) of 0.65 nM, in good agreement with values reported for mammalian brain homogenates (Billard et al. (1984) supra; DeKeyser et al. (1988) supra; Raisman et al. (1985) supra; Reader, T. A. et al. (1989) Naunyn-Schmiedeberg's Arch. Pharmacol. 340: 617–25). This dissociation constant is nearly identical to that previously reported for the cloned D$_1$ receptor expressed in Cos-7 cells, K$_d$=0.3–0.6 nM, (Dearry et al. (1990) supra; Sunahara et al. (1990) supra; Zhou et al. (1990) supra).

Pharmacological characterization of the GL-30 clone showed binding of [$^3$H]SCH-23390 to a site which clearly exhibited a D$_1$-like pharmacology (Table 1). The rank order of potencies of dopaminergic antagonists in displacing the binding shows that the most potent compounds are those previously identified as having the highest affinity for the D$_1$ site (e.g. SCH-23390, cis-flupenthixol and (+) butaclamol). Among other drugs classified as dopamine receptor antagonists, bulbocapnine, haloperidol and clozapine yielded $K_i$ values comparable to those reported for the $D_1$ receptor in native rat and human brain tissues, and for Cos-7 cells transiently transfected with the previously cloned $D_1$ gene. The largest difference found between the affinities of antagonists for this newly cloned receptor and those reported for the previously cloned $D_1$ receptor was for (+) butaclamol which was 6–18 fold less potent at the dopamine $D_{1\beta}$ receptor. Antagonist competition curves were of uniformly steep slope ($n_H \approx 1.0$) suggesting the presence of a single $D_1$ dopamine receptor. The low affinity of (−) sulpiride and quinpirole to displace [$^3$H]SCH-23390 binding is congruent with the $D_2$ selectivity of such drugs. The biogenic amine neurotransmitters serotonin and norepinephrine were inactive in inhibiting the binding of the antagonist radioligand.

In contrast to the data on antagonist binding, the rank order of potencies and apparent dissociation constants obtained for dopaminergic agonists did not display a high degree of correlation with those found in active brain tissues, in peripheral preparations, or in the previously characterized $D_1$ receptor clone. Dopamine displaced [$^3$H]SCH-23390 binding with ≈10–20 fold higher affinity ($K_i$=159 nM) than that reported for $D_1$ receptors in either the brain or in the periphery under the assay condition used. The competition curve for dopamine in these experiments had a relatively shallow slope, indicating the existence of both high and low affinity binding components. The assay conditions were chosen to match those used in assays of the previously cloned $D_1$ receptor, and are expected to promote the low affinity configuration of the receptor. Although this dopamine $D_{1\beta}$ receptor has pharmacological and functional properties similar to $D_1$ receptors previously characterized in the brain and the periphery, its agonist profile makes it a unique receptor.

Cos-7 cells transfected with clone GL-30 exhibited dopamine stimulated cAMP production at a level 13 fold above the basal rate. This effect of dopamine was blocked by the $D_1$ selective antagonist SCH-23390. The $D_1$ selective partial agonist SKF-38393 stimulated cAMP accumulation to a lesser extent than dopamine itself, consistent with its role as a partial agonist (Andersen et al. (1987) supra). The previously cloned $D_1$ receptor was also shown to be coupled to stimulation of adenylate cyclase activity. The observation that the two different $D_1$ receptor genes encode proteins which functionally couple to the same second messenger pathway reinforces the close relationship shown in their amino acid sequences and pharmacological binding profiles. The existence of two separate genes with similar pharmacology and second messenger coupling suggests that their physiological roles may differ in some other aspect, such as tissue or cell-type distribution, synaptic localization (postsynaptic v. presynaptic autoreceptor), or developmental regulation.

Using gene specific primers for PCR amplification of RNA, the distribution of messenger RNA encoding the dopamine $D_{1\beta}$ receptor was examined. The dopamine $D_{1\beta}$ receptor was found to be widely distributed in a variety of higher brain centers, including brainstem, choroid plexus and hippocampus, suggesting a diverse role in regulating brain functions.

Clone GL-30 is an example of a G protein-coupled receptor whose entire coding region is contained within a single exon, similar to the dopamine $D_1$ receptor (Dearry et al. (1990) supra; Monsma et al. (1990) supra; Sunahara et al. (1990) supra; Zhou et al. (1990) supra) and many other members of this superfamily. In contrast, the coding regions of the dopamine $D_2$ and $D_3$ receptors are interrupted by several introns (Bunzow et al., 1988; Sokoloff et al., 1990). Other subfamilies of G protein-coupled receptors (e.g. $\alpha_1$ or $\alpha_2$ adrenergic receptors), which consist of closely related subtypes, also share an intron-containing ($\alpha_1$) or intronless nature ($\alpha_2$) (Regan and Cotecchia, in press). Based upon this similarity in intron-exon organization, as well as the close amino acid homology to the previously cloned $D_1$ receptor, pharmacological binding properties, and second messenger coupling, clone GL-30 can best be characterized as a dopamine $D_1$ receptor.

What is claimed is:

1. An isolated nucleic acid encoding a human dopamine $D_{1\beta}$ receptor, wherein the human $D_{1\beta}$ receptor has the amino acid sequence shown in Seq. I.D. No. 2.

2. An isolated nucleic acid encoding a human dopamine $D_{1\beta}$ receptor having an amino acid sequence identical to that encoded by a nucleic acid sequence contained in plasmid pdopD1-GL-30 (ATCC Accession No. 40839).

3. An isolated nucleic acid of claim 1 or 2, wherein the nucleic acid is DNA.

4. A recombinant vector comprising the nucleic acid of claim 1 or 2.

5. A vector of claim 4 adapted for expression in a bacterial cell which comprises the regulatory elements necessary for expression of the nucleic acid in the bacterial cell so located relative to the nucleic acid encoding the human dopamine $D_{1\beta}$ receptor as to permit expression thereof.

6. A vector of claim 4 adapted for expression in a yeast cell which comprises the regulatory elements necessary for expression of the nucleic acid in the yeast cell so located relative to the nucleic acid encoding the human dopamine $D_{1\beta}$ receptor as to permit expression thereof.

7. A vector of claim 4 adapted for expression in a mammalian cell which comprises the regulatory elements necessary for expression of the nucleic acid in the mammalian cell so located relative to the nucleic acid encoding the human dopamine $D_{1\beta}$ receptor as to permit expression thereof.

8. A plasmid comprising the vector of claim 4.

9. A plasmid of claim 8 adapted for expression in a mammalian cell which comprises the regulatory elements necessary for expression of the nucleic acid in the mammalian cell so located relative to the nucleic acid encoding the human dopamine $D_{1\beta}$ receptor as to permit expression thereof.

10. A plasmid of claim 9 wherein the nucleic acid is DNA.

11. A plasmid of claim 10 wherein the DNA is cDNA.

12. A mammalian cell comprising the plasmid of claim 9.

13. A method for determining whether a chemical compound binds to a human dopamine $D_{1\beta}$ receptor, which comprises contacting a plurality of mammalian cells of claim 12 with the compound under conditions permitting binding of compounds known to bind to a human dopamine $D_{1\beta}$ receptor, and detecting the presence of any compound bound to the human dopamine $D_{1\beta}$ receptor, so as to thereby determine whether the chemical compound binds to the human dopamine $D_{1\beta}$ receptor.

14. A nonneuronal, mammalian cell comprising the plasmid of claim 9.

15. An Ltk-cell comprising the plasmid of claim 9.

16. A nonneuronal, mammalian cell comprising the plasmid of claim 8.

17. An Ltk-cell comprising the plasmid of claim 8.

18. A plasmid designated pdopD1-GL-30 (ATCC Accession No. 40839).

19. A recombinant nucleic acid comprising a nucleotide sequence encoding a human dopamine receptor that is the dopamine receptor $D_{1\beta}$, wherein the dopamine receptor encoded therein has the amino acid sequence identified by Seq. I.D. No. 2.

* * * * *